(12) United States Patent
Mullen et al.

(10) Patent No.: US 8,382,000 B2
(45) Date of Patent: Feb. 26, 2013

(54) PAYMENT CARDS AND DEVICES WITH ENHANCED MAGNETIC EMULATORS

(75) Inventors: Jeffrey David Mullen, Pittsburgh, PA (US); David Lambeth, Pittsburgh, PA (US); Bruce Cloutier, Pittsburgh, PA (US)

(73) Assignee: Dynamics Inc., Pittsburgh, PA (US)

( * ) Notice: Subject to any disclaimer, the term of this patent is extended or adjusted under 35 U.S.C. 154(b) by 114 days.

(21) Appl. No.: 12/339,086

(22) Filed: Dec. 19, 2008

(65) Prior Publication Data

US 2009/0159708 A1 Jun. 25, 2009

Related U.S. Application Data

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul.

(Continued)

(51) Int. Cl.
*G06K 19/06* (2006.01)
(52) U.S. Cl. ......... 235/493; 235/449; 235/492; 235/451
(58) Field of Classification Search ............ 713/186
See application file for complete search history.

(56) References Cited

U.S. PATENT DOCUMENTS

| | | | |
|---|---|---|---|
| 4,353,064 A | 10/1982 | Stamm | |
| 4,394,654 A | 7/1983 | Hofmann-Cerfontaine | |
| 4,614,861 A | 9/1986 | Pavlov et al. | |
| 4,667,087 A | 5/1987 | Quintana | |
| 4,701,601 A | 10/1987 | Francini et al. | |
| 4,720,860 A | 1/1988 | Weiss | |
| 4,786,791 A | 11/1988 | Hodama | |
| 4,789,776 A | 12/1988 | Inoue | |
| 4,791,283 A | 12/1988 | Burkhardt | |
| 4,797,542 A | 1/1989 | Hara | |
| 4,902,146 A | 2/1990 | Ishikawa | |
| 5,038,251 A | 8/1991 | Sugiyama et al. | |
| 5,168,520 A | 12/1992 | Weiss | |
| 5,237,614 A | 8/1993 | Weiss | |
| 5,254,843 A | 10/1993 | Hynes et al. | |
| 5,276,311 A | 1/1994 | Hennige | |

(Continued)

FOREIGN PATENT DOCUMENTS

| | | |
|---|---|---|
| EP | 0203683 | 12/1986 |
| GB | 2420098 | 5/2006 |

(Continued)

OTHER PUBLICATIONS

The Bank Credit Card Business. Second Edition, American Bankers Association, Washington, D.C., 1996.

(Continued)

*Primary Examiner* — Thien M Le
*Assistant Examiner* — Sonji Johnson

(57) ABSTRACT

A payment card (e.g., credit and/or debit card) or other device (e.g., mobile telephone) is provided with a magnetic emulator operable to communicate data to a magnetic stripe read-head. Such a magnetic emulator may comprise non-magnetostrictive material such that the magnetic emulator may be fabricated in a wide variety of fabrication processes. Additionally, magnets may be added to amplify the signal of a magnetic emulator. In doing so, a magnetic emulator may provide a large amount of signal while consuming a reduced amount of electrical energy when compared to a magnetic emulator that does not include the presence of one or more magnets.

47 Claims, 18 Drawing Sheets

Related U.S. Application Data

15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(56) References Cited

U.S. PATENT DOCUMENTS

| | | | |
|---|---|---|---|
| 5,347,580 | A | 9/1994 | Molva et al. |
| 5,361,062 | A | 11/1994 | Weiss et al. |
| 5,412,199 | A | 5/1995 | Finkelstein et al. |
| 5,434,398 | A | 7/1995 | Goldberg |
| 5,434,405 | A | 7/1995 | Finkelstein et al. |
| 5,478,994 | A | 12/1995 | Rahman et al. |
| 5,479,512 | A | 12/1995 | Weiss |
| 5,484,997 | A | 1/1996 | Haynes |
| 5,485,519 | A | 1/1996 | Weiss |
| 5,585,787 | A | 12/1996 | Wallerstein |
| 5,591,949 | A | 1/1997 | Bernstein |
| 5,608,203 | A | 3/1997 | Finkelstein et al. |
| 5,623,552 | A | 4/1997 | Lane |
| 5,657,388 | A | 8/1997 | Weiss |
| 5,748,737 | A | 5/1998 | Daggar |
| 5,834,747 | A | 11/1998 | Cooper |
| 5,834,756 | A | 11/1998 | Gutman et al. |
| 5,844,230 | A | 12/1998 | Lalonde |
| 5,856,661 | A | 1/1999 | Finkelstein et al. |
| 5,864,623 | A | 1/1999 | Messina et al. |
| 5,883,377 | A | 3/1999 | Chapin |
| 5,886,874 | A | 3/1999 | Onoda et al. |
| 5,907,142 | A | 5/1999 | Kelsey |
| 5,913,203 | A | 6/1999 | Wong et al. |
| 5,937,394 | A | 8/1999 | Wong et al. |
| 5,955,021 | A | 9/1999 | Tiffany, III |
| 5,955,961 | A | 9/1999 | Wallerstein |
| 5,956,699 | A | 9/1999 | Wong et al. |
| 6,012,636 | A | 1/2000 | Smith |
| 6,022,761 | A | 2/2000 | Grupen-Shemansky et al. |
| 6,025,054 | A | 2/2000 | Tiffany, III |
| 6,045,043 | A | 4/2000 | Bashan et al. |
| 6,076,163 | A | 6/2000 | Hoffstein et al. |
| 6,085,320 | A | 7/2000 | Kaliski |
| 6,095,416 | A | 8/2000 | Grant et al. |
| 6,129,277 | A | 10/2000 | Grant et al. |
| 6,130,621 | A | 10/2000 | Weiss |
| 6,145,079 | A | 11/2000 | Mitty et al. |
| 6,157,920 | A | 12/2000 | Jakobsson et al. |
| 6,161,181 | A | 12/2000 | Haynes, III et al. |
| 6,176,430 | B1 | 1/2001 | Finkelstein et al. |
| 6,182,894 | B1 | 2/2001 | Hackett et al. |
| 6,189,098 | B1 | 2/2001 | Kaliski |
| 6,199,052 | B1 | 3/2001 | Mitty et al. |
| 6,206,293 | B1 | 3/2001 | Gutman et al. |
| 6,240,184 | B1 | 5/2001 | Huynh et al. |
| 6,241,153 | B1 | 6/2001 | Tiffany, III |
| 6,256,873 | B1 | 7/2001 | Tiffany, III |
| 6,269,163 | B1 | 7/2001 | Rivest et al. |
| 6,286,022 | B1 | 9/2001 | Kaliski et al. |
| 6,308,890 | B1 | 10/2001 | Cooper |
| 6,313,724 | B1 | 11/2001 | Osterweil |
| 6,389,442 | B1 | 5/2002 | Yin et al. |
| 6,393,447 | B1 | 5/2002 | Jakobsson et al. |
| 6,398,115 | B2 | 6/2002 | Krause |
| 6,402,029 | B1 | 6/2002 | Gangi |
| 6,411,715 | B1 | 6/2002 | Liskov et al. |
| 6,446,052 | B1 | 9/2002 | Juels |
| 6,460,141 | B1 | 10/2002 | Olden |
| 6,592,044 | B1 | 7/2003 | Wong et al. |
| 6,594,506 | B1 | 7/2003 | Vapaakaski et al. |
| 6,607,127 | B2 | 8/2003 | Wong |
| 6,609,654 | B1 | 8/2003 | Anderson et al. |
| 6,631,849 | B2 | 10/2003 | Blossom |
| 6,655,585 | B2 | 12/2003 | Shinn |
| 6,681,988 | B2 | 1/2004 | Stack et al. |
| 6,705,520 | B1 | 3/2004 | Pitroda et al. |
| 6,722,031 | B2 | 4/2004 | Japp et al. |
| 6,755,341 | B1 | 6/2004 | Wong et al. |
| 6,764,005 | B2 | 7/2004 | Cooper |
| 6,769,618 | B1 | 8/2004 | Finkelstein |
| 6,783,620 | B1 | 8/2004 | Smith et al. |
| 6,789,298 | B1 | 9/2004 | Fillion et al. |
| 6,801,438 | B1 | 10/2004 | Castro |
| 6,805,288 | B2 | 10/2004 | Routhenstein et al. |
| 6,811,082 | B2 | 11/2004 | Wong |
| 6,813,354 | B1 | 11/2004 | Jakobsson et al. |
| 6,815,523 | B2 | 11/2004 | Yokota |
| 6,817,532 | B2 | 11/2004 | Finkelstein |
| 6,849,934 | B2 | 2/2005 | Ogawa et al. |
| 6,859,115 | B2 | 2/2005 | Hirsch et al. |
| 6,873,974 | B1 | 3/2005 | Schutzer |
| 6,902,116 | B2 | 6/2005 | Finkelstein |
| 6,970,070 | B2 | 11/2005 | Juels et al. |
| 6,980,969 | B1 | 12/2005 | Tuchler et al. |
| 6,985,583 | B1 | 1/2006 | Brainard et al. |
| 6,991,155 | B2 | 1/2006 | Burchette, Jr. |
| 7,013,030 | B2 | 3/2006 | Wong et al. |
| 7,035,443 | B2 | 4/2006 | Wong |
| 7,039,223 | B2 | 5/2006 | Wong |
| 7,044,394 | B2 | 5/2006 | Brown |
| 7,051,929 | B2 | 5/2006 | Li |
| 7,083,094 | B2 | 8/2006 | Cooper |
| 7,097,108 | B2 | 8/2006 | Zellner et al. |
| 7,100,049 | B2 | 8/2006 | Gasparini et al. |
| 7,100,821 | B2 | 9/2006 | Rasti |
| 7,111,172 | B1 | 9/2006 | Duane et al. |
| 7,114,652 | B2 | 10/2006 | Moullette et al. |
| 7,136,514 | B1 | 11/2006 | Wong |
| 7,140,550 | B2 | 11/2006 | Ramachandran |
| 7,163,153 | B2 | 1/2007 | Blossom |
| 7,195,154 | B2 | 3/2007 | Routhenstein |
| 7,197,639 | B1 | 3/2007 | Juels et al. |
| 7,219,368 | B2 | 5/2007 | Juels et al. |
| 7,225,537 | B2 | 6/2007 | Reed |
| 7,225,994 | B2 | 6/2007 | Finkelstein |
| 7,246,752 | B2 | 7/2007 | Brown |
| 7,298,243 | B2 | 11/2007 | Juels et al. |
| 7,334,732 | B2 | 2/2008 | Cooper |
| 7,337,326 | B2 | 2/2008 | Palmer et al. |
| 7,346,775 | B2 | 3/2008 | Gasparinl et al. |
| 7,356,696 | B1 | 4/2008 | Jakobsson et al. |
| 7,357,319 | B1 | 4/2008 | Liu et al. |
| 7,359,507 | B2 | 4/2008 | Kaliski |
| 7,360,688 | B1 | 4/2008 | Harris |
| 7,363,494 | B2 | 4/2008 | Brainard et al. |
| 7,380,710 | B2 | 6/2008 | Brown |
| 7,398,253 | B1 | 7/2008 | Pinnell |
| 7,404,087 | B2 | 7/2008 | Teunen |
| 7,424,570 | B2 | 9/2008 | D'Albore et al. |
| 7,427,033 | B1 | 9/2008 | Roskind |
| 7,454,349 | B2 | 11/2008 | Teunen et al. |
| 7,461,250 | B1 | 12/2008 | Duane et al. |
| 7,461,399 | B2 | 12/2008 | Juels et al. |
| 7,472,093 | B2 | 12/2008 | Juels |
| 7,472,829 | B2 | 1/2009 | Brown |
| 7,494,055 | B2 | 2/2009 | Fernandes et al. |
| 7,502,467 | B2 | 3/2009 | Brainard et al. |
| 7,502,933 | B2 | 3/2009 | Jakobsson et al. |
| 7,503,485 | B1 | 3/2009 | Routhenstein |
| 7,516,492 | B1 | 4/2009 | Nisbet et al. |
| 7,523,301 | B2 | 4/2009 | Nisbet et al. |
| 7,530,495 | B2 | 5/2009 | Cooper |
| 7,532,104 | B2 | 5/2009 | Juels |
| 7,543,739 | B2 | 6/2009 | Brown et al. |
| 7,559,464 | B2 | 7/2009 | Routhenstein |
| 7,562,221 | B2 | 7/2009 | Nystrom et al. |
| 7,562,222 | B2 | 7/2009 | Gasparini et al. |
| 7,580,898 | B2 | 8/2009 | Brown et al. |
| 7,584,153 | B2 | 9/2009 | Brown et al. |

| | | |
|---|---|---|
| 7,591,416 B2 | 9/2009 | Blossom |
| 7,591,426 B2 | 9/2009 | Osterweil et al. |
| 7,591,427 B2 | 9/2009 | Osterweil |
| 7,602,904 B2 | 10/2009 | Juels et al. |
| 7,621,458 B2 | 11/2009 | Zellner et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,681,232 B2 | 3/2010 | Nordentoft et al. |
| 7,828,207 B2 | 11/2010 | Cooper |
| 7,954,724 B2 * | 6/2011 | Poidomani et al. ......... 235/492 |
| 2001/0034702 A1 | 10/2001 | Mockett et al. |
| 2001/0047335 A1 | 11/2001 | Arndt et al. |
| 2002/0003169 A1 | 1/2002 | Cooper |
| 2002/0043566 A1 | 4/2002 | Goodman et al. |
| 2002/0047049 A1 | 4/2002 | Perron et al. |
| 2002/0059114 A1 | 5/2002 | Cockrill et al. |
| 2002/0082989 A1 | 6/2002 | Fife et al. |
| 2002/0096570 A1 | 7/2002 | Wong et al. |
| 2002/0120583 A1 | 8/2002 | Keresman, III et al. |
| 2002/0153424 A1 | 10/2002 | Li |
| 2003/0034388 A1 | 2/2003 | Routhenstein et al. |
| 2003/0052168 A1 | 3/2003 | Wong |
| 2003/0057278 A1 | 3/2003 | Wong |
| 2003/0111527 A1 | 6/2003 | Blossom |
| 2003/0116635 A1 | 6/2003 | Taban |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0209608 A1 | 11/2003 | Blossom |
| 2003/0218066 A1 | 11/2003 | Fernandes et al. |
| 2003/0226899 A1 | 12/2003 | Finkelstein |
| 2004/0011877 A1 | 1/2004 | Reppermund |
| 2004/0035942 A1 | 2/2004 | Silverman |
| 2004/0133787 A1 | 7/2004 | Doughty |
| 2004/0159700 A1 | 8/2004 | Khan et al. |
| 2004/0162732 A1 | 8/2004 | Rahim et al. |
| 2004/0172535 A1 | 9/2004 | Jakobsson |
| 2004/0177045 A1 | 9/2004 | Brown |
| 2004/0206829 A1 | 10/2004 | Welling et al. |
| 2005/0001711 A1 | 1/2005 | Doughty et al. |
| 2005/0043997 A1 | 2/2005 | Sahota et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0092830 A1 | 5/2005 | Blossom |
| 2005/0116026 A1 | 6/2005 | Burger et al. |
| 2005/0119940 A1 | 6/2005 | Concilio et al. |
| 2005/0133590 A1 | 6/2005 | Rettenmyer et al. |
| 2005/0154643 A1 | 7/2005 | Doan et al. |
| 2005/0178827 A1 | 8/2005 | Shatford |
| 2005/0194452 A1 | 9/2005 | Nordentoft et al. |
| 2005/0218229 A1 | 10/2005 | Morley et al. |
| 2005/0219728 A1 | 10/2005 | Durbin et al. |
| 2005/0228959 A1 | 10/2005 | D'Albore et al. |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0091223 A1 | 5/2006 | Zellner |
| 2006/0131393 A1 | 6/2006 | Cok et al. |
| 2006/0131410 A1 | 6/2006 | Fernandes et al. |
| 2006/0161435 A1 | 7/2006 | Atef et al. |
| 2006/0161789 A1 * | 7/2006 | Doughty et al. ......... 713/186 |
| 2006/0163353 A1 | 7/2006 | Moulette et al. |
| 2006/0174104 A1 | 8/2006 | Crichton et al. |
| 2006/0186209 A1 | 8/2006 | Narendra et al. |
| 2006/0196931 A1 | 9/2006 | Holtmanns et al. |
| 2006/0227523 A1 | 10/2006 | Pennaz et al. |
| 2006/0249574 A1 | 11/2006 | Brown et al. |
| 2006/0256961 A1 | 11/2006 | Brainard et al. |
| 2006/0261174 A1 | 11/2006 | Zellner et al. |
| 2006/0283958 A1 | 12/2006 | Osterweil |
| 2007/0017975 A1 | 1/2007 | Lewis et al. |
| 2007/0023532 A1 | 2/2007 | Narendra et al. |
| 2007/0034700 A1 * | 2/2007 | Poidomani et al. ......... 235/492 |
| 2007/0114274 A1 | 5/2007 | Gibbs et al. |
| 2007/0124321 A1 | 5/2007 | Szydlo |
| 2007/0136211 A1 | 6/2007 | Brown et al. |
| 2007/0138299 A1 | 6/2007 | Mitra |
| 2007/0152070 A1 | 7/2007 | D'Albore |
| 2007/0152072 A1 | 7/2007 | Fralicciardi et al. |
| 2007/0153487 A1 | 7/2007 | Fralicciardi et al. |
| 2007/0174614 A1 | 7/2007 | Duane et al. |
| 2007/0192249 A1 | 8/2007 | Biffle et al. |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0093467 A1 | 4/2008 | Narendra et al. |
| 2008/0096326 A1 | 4/2008 | Reed |
| 2008/0121726 A1 | 5/2008 | Brady et al. |
| 2008/0126260 A1 | 5/2008 | Cox et al. |
| 2008/0126398 A1 | 5/2008 | Cimino |
| 2008/0128515 A1 | 6/2008 | Di Iorio |
| 2008/0148394 A1 | 6/2008 | Poidomani et al. |
| 2008/0201264 A1 | 8/2008 | Brown et al. |
| 2008/0209550 A1 | 8/2008 | Di Iorio |
| 2008/0288699 A1 | 11/2008 | Chichierchia |
| 2008/0290166 A1 | 11/2008 | von Mueller |
| 2008/0294930 A1 | 11/2008 | Varone et al. |
| 2008/0302877 A1 | 12/2008 | Musella et al. |
| 2009/0006262 A1 | 1/2009 | Brown et al. |
| 2009/0013122 A1 | 1/2009 | Sepe et al. |
| 2009/0036147 A1 | 2/2009 | Romano |
| 2009/0046522 A1 | 2/2009 | Sepe et al. |
| 2009/0048971 A1 | 2/2009 | Hathaway et al. |
| 2009/0108064 A1 | 4/2009 | Fernandes et al. |
| 2009/0150295 A1 | 6/2009 | Hatch et al. |
| 2009/0152365 A1 | 6/2009 | Li et al. |
| 2009/0159701 A1 | 6/2009 | Mullen |
| 2009/0159708 A1 | 6/2009 | Mullen |
| 2009/0173782 A1 | 7/2009 | Muscato |
| 2009/0240592 A1 | 9/2009 | Baumgart et al. |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0290704 A1 | 11/2009 | Cimino |
| 2009/0303885 A1 | 12/2009 | Longo |
| 2010/0084476 A1 | 4/2010 | Zellner et al. |
| 2010/0270373 A1 | 10/2010 | Poidomani et al. |
| 2011/0028184 A1 | 2/2011 | Cooper |

FOREIGN PATENT DOCUMENTS

| | | |
|---|---|---|
| JP | 05210770 A | 8/1993 |
| WO | WO9852735 | 11/1998 |
| WO | WO0247019 | 6/2002 |
| WO | WO2006066322 | 6/2006 |
| WO | WO2006080929 | 8/2006 |
| WO | WO2006105092 | 10/2006 |
| WO | WO2006116772 | 11/2006 |
| WO | WO2007141779 | 12/2007 |
| WO | WO2008064403 | 6/2008 |

OTHER PUBLICATIONS

A Day in the Life of a Flux Reversal. http://www.phrack.org/issues.html?issue=37&id=6#article. As viewed on Apr. 12, 2010.

Dynamic Virtual Credit Card Numbers. http://homes.cerias.purdue.edu/~jtli/paper/fc07.pdf. As viewed on Apr. 12, 2010.

USPTO, International Search Report, Apr. 28, 2009.
U.S. Appl. No. 60/594,300, filed Mar. 2005, Poidomani et al.
U.S. Appl. No. 60/675,388, filed Apr. 2005, Poidomani et al.
English translation of JP 05210770 A, Aug. 1993.

Australian Patent Office, Patent Examination Report No. 1, Oct. 11, 2012.
EPO, Extended European Search Report, Jan. 26, 2012.

* cited by examiner

PAYMENT CARDS AND DEVICES WITH ENHANCED MAGNETIC EMULATORS

CROSS-REFERENCE TO RELATED APPLICATIONS

This application claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches or more) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

A read-head detector, or an array of read-head detectors, may be able to, for example, determine the type of reader that the card entered into. For example, a read-head detector array may determine, for example, when a motorized reader was utilized, an insertion reader was utilized, or a user-swipe reader was utilized. Such information may be stored and communicated to a remote storage device (e.g., a remote database). This stored information may be utilized to combat, for example, card cloning. For example, if a particular number of cards (e.g., 10 more) that made consecutive purchases from a machine (e.g., an ATM) detected more than one reader, then, for example, the system may make an autonomous determination that an illegal cloning device was located on front of that ATM machine. If, for example, multiple cards use a restaurant point-of-sale terminal and determine that multiple readers were used then, for example, a computer can make an autonomous determination that cloning may have occurred at the restaurant.

A material may be sandwiched between the two layers to assist in reducing the effect of the electromagnetic fields from one set of coil segments on the side of the material opposite that set of coil segments. Such an interior material may be insulated such that the material does not short the coil segments. Additionally, such an interior material may be chosen, for example, such that the material does not saturate when the coil is conducting current. The coil and material may run, for example, along the location of a track of magnetic data for a payment card. Accordingly, a coil may be fabricated so that the coil wraps around an interior material.

A material may be placed and/or printed on a PCB layer and sandwiched between two other PCB layers. These two other layers may each include coil segments and vias. The middle layer may also include vias such that the material is fabricated to be located in the center of the coil. The material may take a cylindrical, rectangular, square, or any type of shape. Four layers may also be utilized, where the coil segments are printed on a surface of the exterior layers and one or more materials are printed and/or placed on/between the interior layers. A material may be a magnetic material, ferromagnetic material, ferrimagnetic material, or any type of material. For example, copper may be printed on a PCB layer and plated with a material (e.g., nickel, iron, chrome, tin, gold, platinum, cobalt, zinc, alloys). A material, for example, may have a relative permeability multiple times greater than the permeability of a vacuum. A material, for example, may have a relative permeability of 2 to 100 to 25,000. A material may include, for example, a permalloy, iron, steel, ferrite, nickel or any other material (e.g., any soft magnetic material). A material may be an alloy such as a nickel-iron alloy. Such a nickel-iron alloy may include, for example, nickel (e.g., 75-85%), iron, copper, molybdenum and may be placed through one or more annealing processes. Annealing may occur before and/or after the material is placed/printed on a layer of material (e.g., a PCB or other layer). A similar and/or different material may be placed either above and/or below a portion, or the entire, set of paths on a layer for a coil. Accordingly, for example, a material may be placed in the interior of a coil as well as along a side of the coil.

Displays may be provided near user interfaces or other structures. For example, a display may be provided next to an LED. Cards may be programmed during manufacturing so that these displays may display particular information. Accordingly, for example, the same card architecture may be utilized to provide a number of different types of cards. A user may utilize user interfaces (e.g., mechanical or capacitive interfaces) to change the function of the display. For example, codes may be entered to reconfigure the displays. Alternatively, for example, a user may utilize buttons to select information to be displayed on displays associated with user interfaces. A code may associate a name of a store with a button and/or a dollar amount. For example, a display may be configured to read "Target $50." Information may be entered manually, but also may be received by a card. For example, a user may swipe a card a second time through a magnetic stripe reader and receive information via a magnetic emulator. This received information may be utilized to update information on the card (e.g., the balance of a gift card, credit account, and/or debit account). Information may also be received by an RFID antenna and/or IC chip located on a card and in communication with a central processor (or distributed processors). For example, transaction information (e.g., list of past transactions, stores where transactions occurred, amounts of transactions) and account information (e.g., balance information, bill information, amount due information) may be communicated to the card and displayed on one or more displays.

A dynamic card may be manufactured in a variety of ways. For example, a dynamic card may be printed onto a flexible material (e.g., a flexible polymer). Multiple layers of this material may be bonded together to form a multiple layer flexible structure. This multiple layer structure may be laminated (e.g., via hot, warm and/or cold lamination) to form a card. The card may be programmed before or after lamination. A card may be programmed via a direct connection between a programmer and one or more contacts on a card. A card may be programmed via a capacitive, optical, or inductive communication via a communication link between a programmer and one or more communication components on a card. Accordingly, for example, a card may be laminated and capacitively, optically, or inductively programmed. After programming, a processor on the card may be signaled to burn-out its programming communication channel(s) such that no further programming may occur. A portion of the card may not be laminated. Accordingly, a programmer may connect to this non-laminated portion of the card. The non-laminated portion of the card may be laminated after programming. Alternatively, for example, the non-laminated portion of the card may be cut after programming (e.g., and after the processor burns-out its programming ports so the processor cannot be further programmed).

Additional external communication devices may be provided on a card. For example, a USB port or Wi-Fi antenna may be provided on a card. Such additional external communication devices may, for example, allow a user to communicate with stationary computer, laptop, or other device. Such communication devices may, for example, be utilized to load gift cards, or other information (e.g., transactional or account information) from a laptop to a card or other device. A card is provided that includes a light sensor such that information can be communicated to a card via light (e.g., via a light transmitted from a TV or website).

A magnetic emulator may produce an electromagnetic field that is operable to be read by a magnetic stripe reader. Such a magnetic emulator may include a coil. Current may be provided through such a coil such that an electromagnetic signal is produced. Material may be placed inside the coil with a permeability that results in an increase of the electromagnetic signal about the exterior of the coil. Such a material may be, for example, a soft-magnetic material (e.g., a permalloy). Such a soft-magnetic material may not be able to, for example, be permanently magnetized.

A magnetic emulator having a coil with a soft-magnetic interior may be fabricated in a printed circuit board process (e.g., using an FR4 board material). In doing so, for example, the electromagnetic field located about the exterior of the coil may be increased by the presence of the soft-magnetic interior.

Magnetostrictive materials may be provided about the interior of a coil. Magnetostrictive materials may mechanically distort in response to a magnetic field. This mechanical distortion may, in turn, affect the magnetic field. Magnetic emulators are provided with coils having magnetostrictive interior materials. An aperture may be cut into a printed circuit board layer such that the magnetostrictive material is operable to mechanically distort within the aperture while in a multiple layer printed circuit board.

Non-magnetostrictive material may be utilized as an interior material for a coil operable to communicate data to a magnetic stripe reader. Such a non-magnetostrictive material may have zero parts per million of magnetostrictive elements or may have a low amount of magnetostriction (e.g., less than 200 parts per million).

A permanent magnet may be placed about a magnetic emulator. For magnetic emulators that include one or more coils, a permanent magnet may be placed about the interior, or exterior, of one of the coils. Such a permanent magnetic may provide, for example, a bias magnetic field that may increase the amount of electromagnetic field present about the exterior of a coil. A bias field may also be created, for example, via a coil (e.g., a coil about a magnetic emulator).

A magnetic emulator may include one or more coils that include both a soft-magnetic material and a permanent magnet.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which.

DETAILED DESCRIPTION OF THE INVENTION

Figure 1:
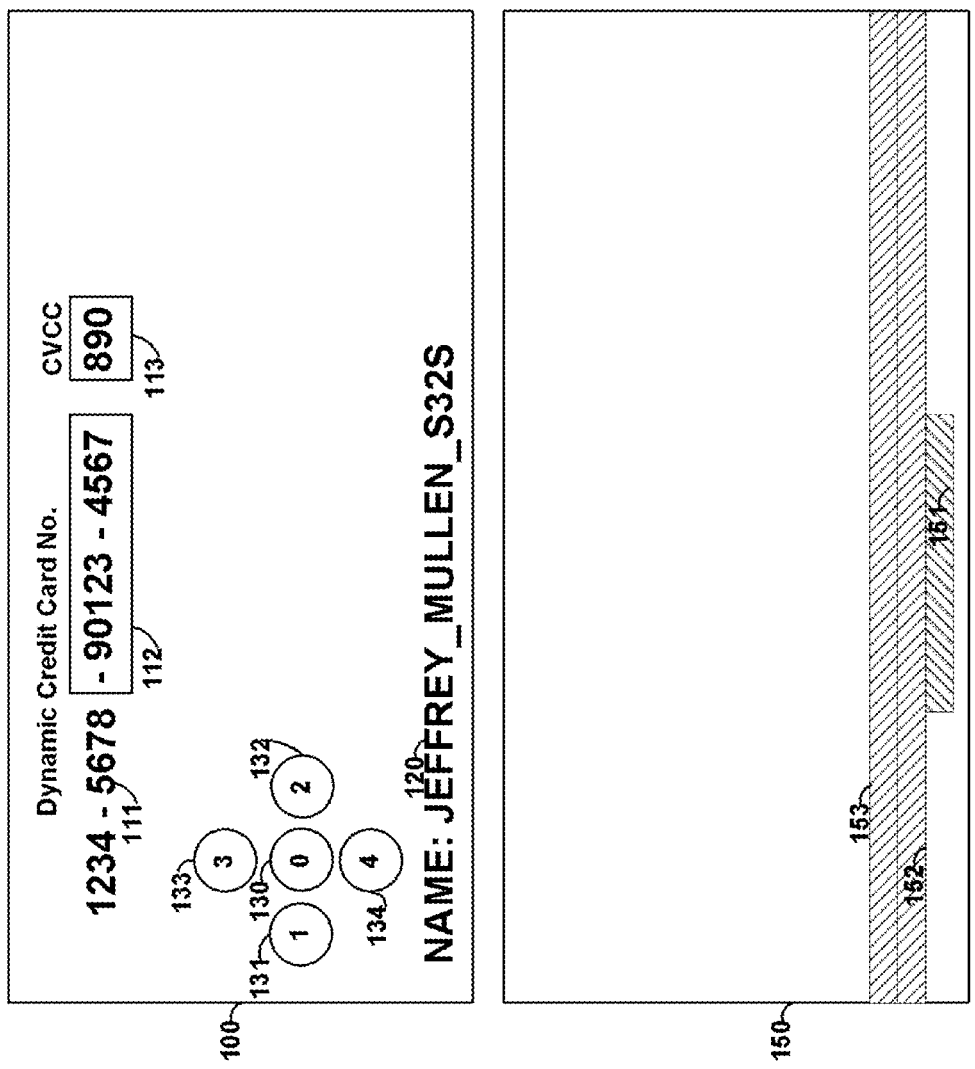
FIG. 1 is an illustration of cards constructed in accordance with the principles of the present invention.

FIG. 1 shows card 100 that includes printed information 111 and 120, displays 112 and 113, and buttons 130-134.

Card 100 may be, for example, a payment card such as a credit card, debit card, and/or gift card or any other type of card (e.g., security access or identification card). Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identified using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. Magnetic emulator 151 may be included and may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader.

For example, credit card information may be transmitted to a magnetic stripe reader at speeds up to, and greater than, 30 kHz.

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Emulator 151 may be included such that dynamic information may be communicated to a magnetic stripe reader, for example, without a magnetic stripe via an electromagnetic signal transmitted directly from emulator 151 to a read-head of a magnetic stripe reader. Any combination of emulators and static magnetic tracks may be utilized for a card or device (e.g., two magnetic emulators without any magnetic stripes).

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
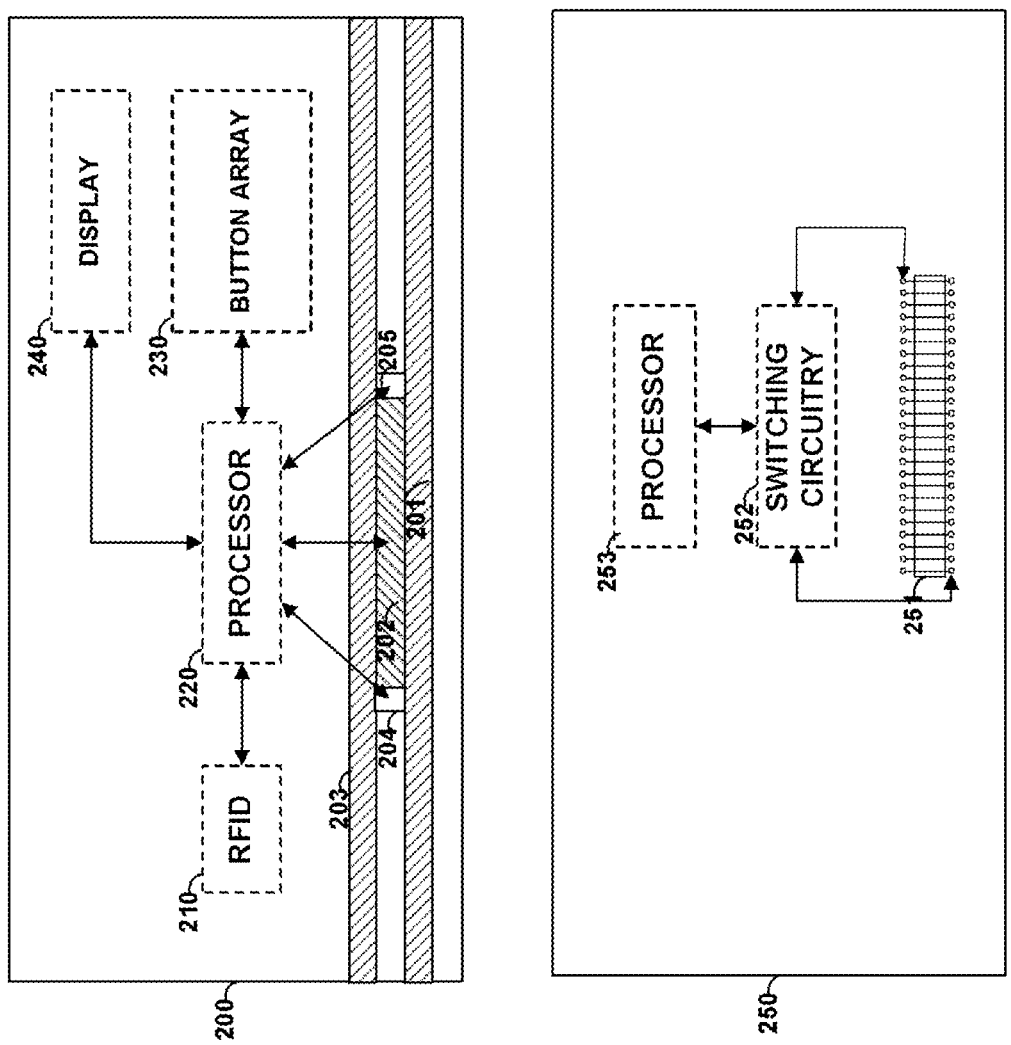
FIG. 2 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202. Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230. A smart-card chip may, for example, be included on card 200 in lieu of, or in addition to, RFID 210.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes a coil operable to communicate data serially to a magnetic stripe reader. Similarly, for example, emulator 251 may receive information for a magnetic stripe encoder. Persons skilled in the art will appreciate that a coil may run across the length of a card such that a read-head moves along the length of the coil and can receive information transmitted serially from the coil. The coil may extend into multiple tracks such that multiple read-heads receive information from the coil. Track information can be sent serially (e.g., track 1 information followed by track 2 information). Multiple coils may be driven separately and placed in different zones such that a single read-head moves from coil-to-coil (e.g., zone-to-zone) and power is conserves as only coils in a particular zone (or zones) may be utilized to communicate information any particular time. Separate coils may be utilized for separate tracks. Materials may be placed in the interior of each coil to assist with manipulating the electromagnetic field produced by the coils. Material may be placed above or below a coil to further manipulate the electromagnetic field produced by the coil. Switching circuitry 252 may include, for example, one or more transistors that may be utilized to control the direction of current via emulator 251 (e.g., the polarity of voltage(s) across a drive resistor). For example, a coil may be utilized to transmit a string of information to a particular read-head. Different coils may transmit information at different speeds (or at the same speed). Different coils may transmit different amounts of information. For example, three coils may be provided. The coil closest to the bottom of the long-end of a card may transmit at least 79 characters. The coil next closest to the bottom of the long-end of a card may transmit at least 40 characters of information. The coil next closest to the bottom of the long-end of the card may transmit at least 107 characters. One or more coils may have different character sets (e.g., a 6-bit character set or a 7-bit character set). The last bit in a character may include, for example, a parity bit. Additional synching information may be transmitted before and after the data information to assist with synching a magnetic stripe reader. For example, a string of zeros may be communicated before and after communicating primary data. Characters may be included in the data information for other purposes such as an LRC character.

Figure 3:
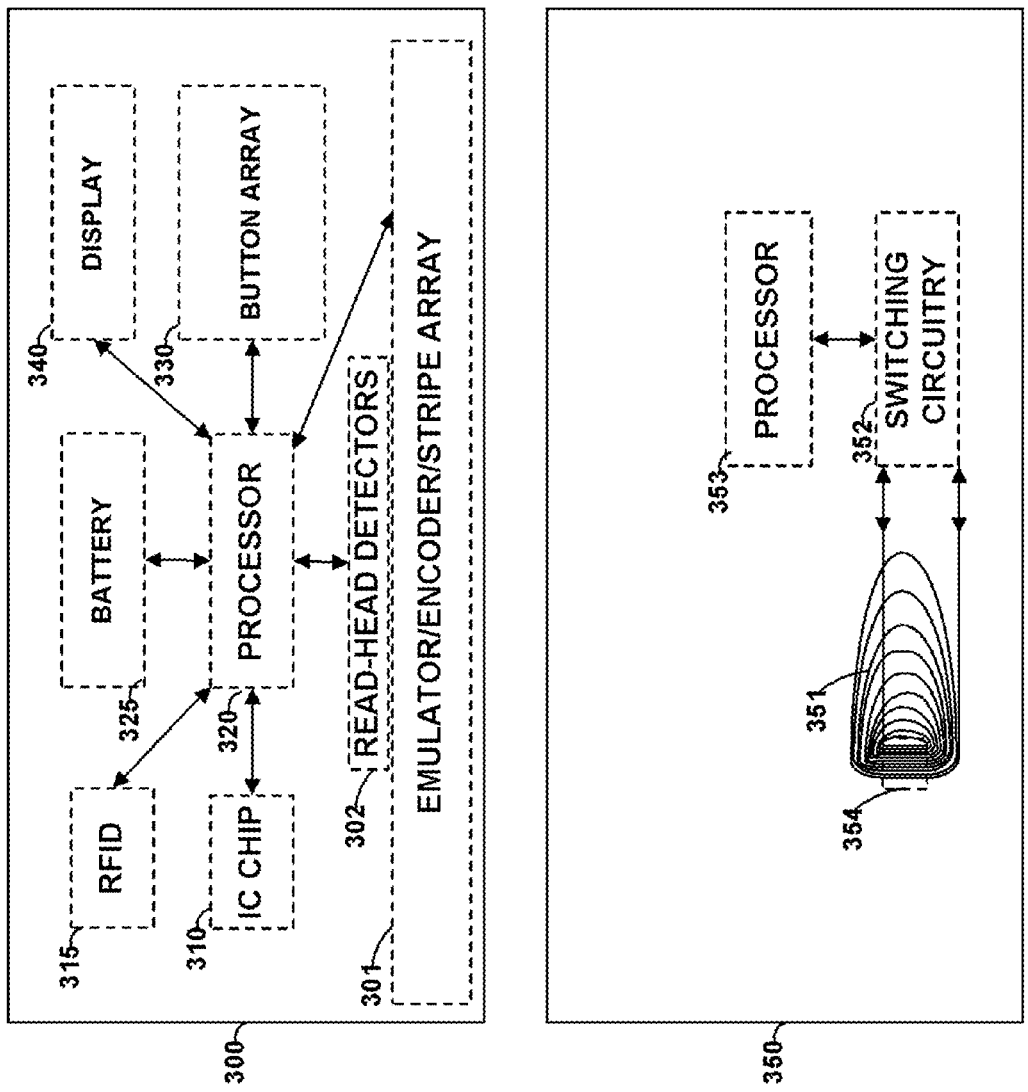
FIG. 3 is an illustration of cards constructed in accordance with the principles of the present invention.

FIG. 3 shows card 300 that may include a number of components. Card 300 may include one or more processors 320. A processor may include, for example, cache memory, RAM, and/or ROM. Additional memory may be provided on card 300. For example, additional non-volatile, volatile, cache memory, RAM, and/or ROM may be provided on card 300. Battery 325 may be provided on card 300. Battery 325 may be, for example, a lithium polymer battery and may have a thickness less than a millimeter (e.g., approximately 0.5 mm). RFID antenna 315 may be provided on card 300 and may communicate data to an RFID reader. Persons skilled in the art will appreciate that an RFID may be included that is a passive or active RFID. IC chip 310 may be included on card 300 and may communicate data to an IC chip reader. Device 301 may be included to communication information to a magnetic stripe reader. Device 301 may include any number of magnetic emulators, magnetic encoders that encode magnetic stripes, and/or magnetic stripes. For example, device 301 may include a magnetic emulator for one track of magnetic data and a magnetic stripe for a second track of data. Alternatively, for example, device 301 may include two emulators for separate tracks of data. An emulator may, for example, communicate information to a read-head of a magnetic stripe reader serially. One or more read-head detectors 302 may be provided to detect a read-head (or other attribute) of a magnetic stripe reader. Additional detectors may be included to detect, for example, when a card is provided into an IC chip reader and/or an electromagnetic field from an RFID reader. Button array 330 may be provided, for example, to receive input from a user. Button array 330 may include any number of buttons (e.g., 4, 5, 10, or more than 10). Button array 330 may include, for example, mechanical buttons, capacitive buttons, or any type of user interface. One or more displays 340 may also be included. A display may be, for example, an electronic ink display (e.g., electrochromic display), LCD display, or any other type of display. Display 340 may be flexible.

Display 340 may be printed onto a layer during a printed fabrication process (e.g., PCB). Additionally, for example, battery 325 may be printed onto a layer during a printed fabrication process (e.g., PCB). Similarly, a magnetic emulator may be printed onto a layer during a printed fabrication process (e.g., PCB). Other components may be printed onto a layer during a printed fabrication process (e.g., PCB) such as capacitive read-head detectors, and capacitive touch sensors. Accordingly, a display, battery, read-head detector, and button array may be printed on one or more layers that are bonded together and laminated.

FIG. 3 shows card 350 that may include, for example, processor 353, switching circuitry 352, and emulator 351 having active region 354. Switching circuitry 352 may, for example, control the direction of current through emulator 351 in order to change the direction of electromagnetic fields generated by emulator 351 such that data may be communicated serially to a magnetic stripe read-head. Persons skilled in the art will appreciate that emulator 351 may be fabricated on a single layer and that region 354 may include coil segments dense enough to generate an electromagnetic field that can be recognized by a read-head of a magnetic stripe reader.

Figure 4:
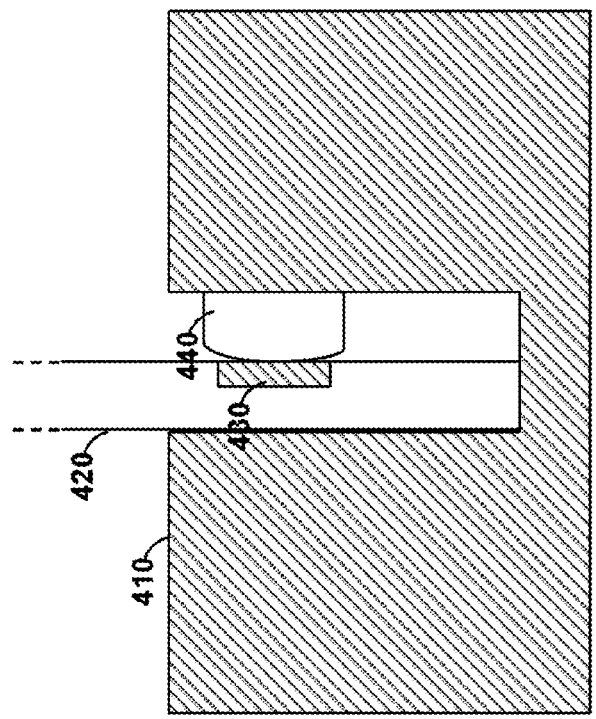
FIG. 4 is an illustration of a card and a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
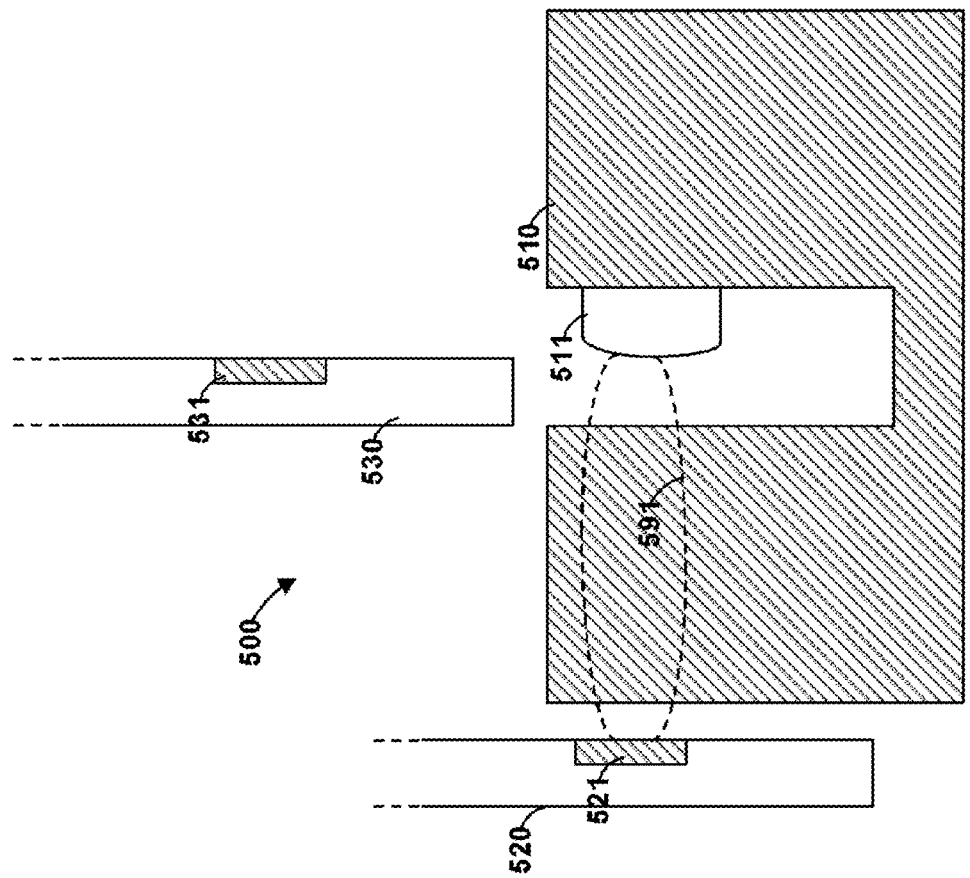
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contactless transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card using, for example, a hot and/or cold lamination. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Persons skilled in the art will appreciate that the direction of current through magnetic circuit 650 may be changed and controlled in a pattern that is representative of magnetic stripe data. Particularly, a processor may, for example, transmit information through a coil by changing the direction of the electromagnetic field generated from emulator circuit at particular times. A change in the frequency of field reversals may be representative of, for example, a particular bit of information (e.g., "1" or "0").

Figure 6:
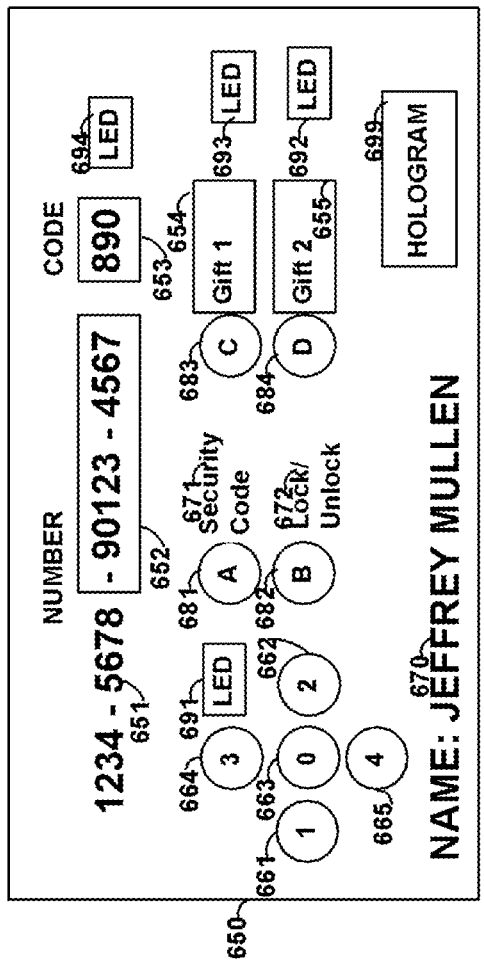
FIG. 6 is an illustration of a card constructed in accordance with the principles of the present invention.

FIG. 6 shows card 650 that includes buttons 651-664, light sources 691-694, displays 852-853, permanent information 651 and 670, buttons 681-684, and hologram 699. A user may be provided with a payment number. Such a payment number may be comprised of permanent data, dynamic data, or a combination of permanent and dynamic data. Dynamic data may be provided, for example, on display 652. Display 653 may be utilized to provide a code, which may be dynamic. Such a code may be utilized in authorize a transaction. Persons skilled in the art will appreciate that displays may display a code, payment number, or any type of data that changes based on time or based on use (e.g., utilizes one-time use data). Similarly, data may be static and may not change. Accordingly, for example, a display may be utilized to display the same data when desired such that the data may be hidden when the data is not desired to be displayed. Buttons 651-664, 681-682, and/or 683-684 may be utilized to signal a processor to display information on display 652, display 643, or display 652 and display 653.

A Personal Identification Code (PAC) may be entered to utilize to display data, as well as instruct a processor to provide particular data. For example, a particular PAC may provide one payment number (e.g., a credit card number) while a different PAC may provide a different payment number (e.g., a debit card number). A PAC may include a sequence of button presses (e.g., 5 particular button presses). Furthermore, a PAC may be utilized to unlock a card so that the card may be utilized. For example, buttons 681, 682, 683, and 684 may not be utilized by a user until an appropriate PAC has been entered via buttons 651-665. A number may be changed based on time (e.g., via display 652, display 653, or display 652 and display 653). Accordingly, a PAC may be entered such that the particular number associated with a particular button (e.g., a number associated with button 651) for a particular time period (e.g., a particular day) may be displayed. One PAC may activate display 652 while another PAC may activate display 653.

Light source 691 may be an LED or other source of light. Light source 691 may display light each time a button associated to light source 691 is pressed (e.g., buttons 661-662). Similarly, light source 692 may display light each time a button associated with light source 692 is pressed (e.g., button 681 or 682). Light source 693 may display light each time a button associated with light source 693 is pressed (e.g., light source 683 or 684). Light source 694 may be associated to a component and may display light each time that component is activated (e.g., display 653 or 652 is activated). Light sources may emit light having different colors. For example, a processor may determine that a PAC provided to the processor via buttons 661-665 matches a valid PAC for performing an operation. Each button press may cause light source 691 to emit light of a first color (e.g., YELLOW). The last button press to complete the PAC, however, may cause light source 691 to emit a different color if the PAC is VALID (e.g., emit GREEN) yet emit another color if the PAC is INVALID (e.g., emit RED). Particular areas of a laminated card may be transparent such that light from a light-source illuminates the transparent area.

Button 681 may be associated with a card of a particular country. Persons skilled in the art will appreciate that a card may be provided with a default number. Such a default number may include, for example, permanent data 651 and data displayed on display 652. Accordingly, a particular PAC may display the default data on display 652.

Persons skilled in the art will appreciate that other default data may be provided to other components of a card upon entry of a PAC. For example, particular default data (e.g., payment card number and discretionary data) may be communicated to a magnetic emulator (or magnetic encoder) such that the information may be communicated to a magnetic stripe read-head. Similarly, default data (e.g., payment card number and discretionary data) may be communicated to an RFID antenna, an IC chip, or an RFID antenna and an IC chip. Such default data may be different for each component (e.g., magnetic encoder/emulator, RFID antenna, IC Chip) and may be in different formats (e.g., one track of payment data for one magnetic emulator and another track of payment data for another magnetic emulator).

Button 681 may cause, for example, display 652, display 653, or display 652 and 653 to display data associated to button 681. Similarly, data associated to button 681 for other components of card 650 (e.g., a magnetic emulator, magnetic encoder, RFID antenna, and IC chip) may be communicated through those components. Button 681 may be associated with, for example a particular territory (e.g., America). Accordingly, for example, information communicated via card 650 may be associated with a default country upon entry of a particular PAC until, for example, a button is pressed associated with a different country. At this time, for example, the information communicated by card 650 may change to the information associated with the particular button pressed. Button 692 may be provided for a country different than, for example, a default country and a country associated with another button (e.g., button 681). A card may not be associated with a default country such that, for example, a button is pressed to determine the type of information communicated by a card.

Button 683 may be utilized to provide instructions to a processor that a gift card is desired to be utilized via card 650. A gift code may be entered (e.g., via buttons 661-665) after button 683 is pressed such that a user may, for example, associate a gift card to card 650. Accordingly, card 650 may be utilized to make a gift purchase such that the original gift card may be thrown out (or left at home). The code entered into card 350 may be utilized, for example, to provide a processor with a number to transmit via the card (e.g., next time button 683 is utilized). Such a number (as well as associated data such as associated discretionary data) may be communicated by card 650 via one or more displays, magnetic emulators, magnetic encoders, RFID antennas, and IC chips. A code may alternatively, for example, transmit a flag (e.g., discretionary data) that a gift card is being utilized (e.g., upon another use of button 683) such that a server may look at a seller ID number and check if there are any gift cards associated to a particular payment card number for that seller ID number. Accordingly, for example, a user may obtain a gift card (e.g., Target gift card) and may link that gift card to his/her payment card account (e.g., credit card account) and may utilize a button (e.g., 683) to send a flag that a gift card is desired to be utilized. A code may be entered to provide a particular flag (e.g., a flag associated with a particular seller). Alternatively, no code may be entered and button 683 may just be utilized to generate a generic flag (e.g., causing a server to check if there are any linked gift cards for the account associated with the seller associated with the utilized point-of-sale reader). A user may be provided with a particular code to be entered when utilize the gift card at an online store (e.g., Target's online store). The online store may, for example, allow a user to enter his/her payment information (e.g., credit card number, expiration date, name on card, zip code associated with card) and allow the user to select whether a gift card should be utilized associated with that card (e.g., via a radio button or other webpage input structure).

Button 684 may be provided. Button 684 may be utilized, for example, to make an in-store purchase. Button 684 may activate, for example, display 652 but not display 653. Code 653 may be utilized, for example, to at least complete a particular online transaction. In not activating display 653, for example, a user that is provided with a card during an in-store purchase may not gain access to information displayed on display 653. Persons skilled in the art will appreciate, for example, that the information on display 653 may be transmitted via a component (e.g., emulator) even though the information is not displayed. Moreover, for example, display 652 and 653 may be the same display but that a particular interface (e.g., button) may display information on different portions of the display.

Button 681 may be associated with a security code such that each time button 681 is pressed, a new security code is displayed (e.g., via display 653). Permanent information 671 may be utilized to describe the functionality of button 681.

Button 682 may be by associated with unlocking and locking a card. A processor (not shown) may look to receive a personal identification code after button 682 is pressed to unlock a card. Similarly, an unlocked card may re-task a number of buttons to perform a variety of functions. Locking a card (e.g., via button 682) may cause those buttons to return to a default state in which a processor (not shown) is looking to receive a personal identification number. Permanent information 672 may be associated with, for example, the functionality of button 682.

Button 683 may be associated with, for example, display 654. Button 683 may be associated with, for example, display 655. The utilization of displays 654 and 655 may be programmed, for example, by a user at any time through the entry of a reconfiguration code. For example, a user may load multiple gift cards into his/her payment card and associate each payment card with a different display and associated button. Light source 693 may activate when button 683 is pressed by a user. Light source 692 may activate when button 684 is pressed by a user.

Figure 7:
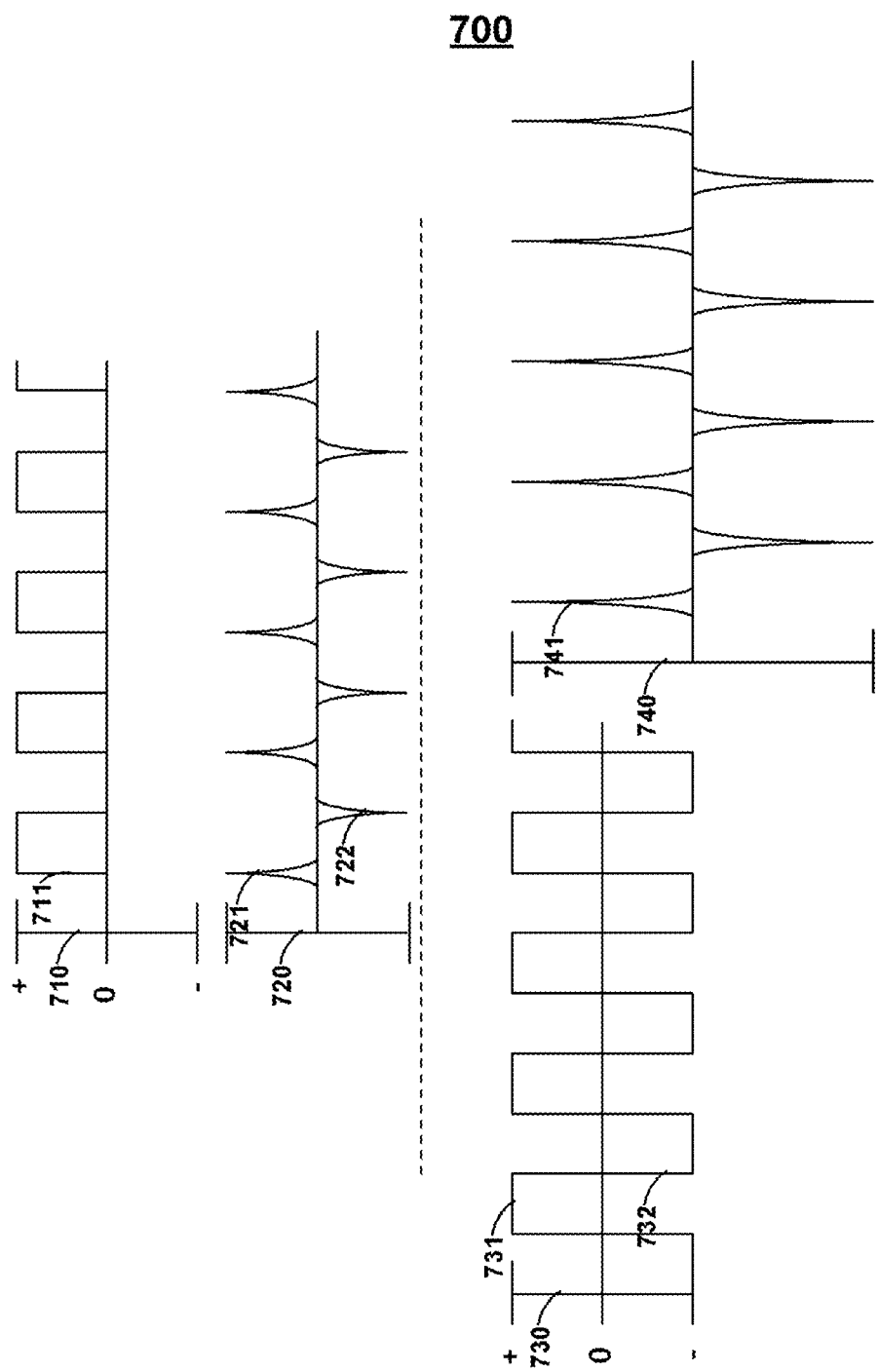
FIG. 7 is an illustration of control signals and magnetic stripe reader sense signals constructed in accordance with the principles of the present invention.

FIG. 7 shows control signals 710 and 720 and magnetic stripe reader sense signals 730 and 740. Control signals 710 may be utilized to drive, for example, a magnetic emulator serially communicating data to a magnetic stripe reader. A magnetic emulator may be, for example, driven by a current having a positive polarity or being able to swing between a positive and a negative polarity. Such a current may be generated, for example, from a transistor providing a drive voltage over a drive resistor. An H-bridge may be utilized, for example, to drive current through a coil in both directions.

Range 710 shows current signal 711 that is provided in a single polarity. A magnetic stripe reader may read the timing of phase transversals to determine whether a one ("1") or a zero ("0") was received. For example, a short period of time before a phase transversal may be determined to be a particular bit of information while a long period of time before a phase transversal may be a different bit of information. Information may be encoded using, for example, F2F encoding such that a magnetic stripe reader may be configured to perform F2F decoding to extract information.

Range 720 shows signal 721, which may be the signal sensed by a magnetic stripe reader. Persons skilled in the art will appreciate that signal 721. Signal 721 may, for example, be provided as a series of pulses. An increase of current through an emulator may, for example, correspond to a positive pulse and a decrease of current through an emulator may, for example, correspond to a negative pulse. The magnitude of a magnetic stripe reader sense pulse may, for example, be correlated with the rate of change of the drive signal of a magnetic stripe emulator. Accordingly, for example, a larger rate of change may correlate to larger sense pulses. Information may be determined at the reader by, for example, F2F decoding. Persons skilled in the art will appreciate that, for example, a longer period of a pulse may lengthen the distance between pulses. Decoding may, for example, determine a swipe rate (e.g., by looking at a string of leading zero bits). A logic zero may provide pulses that define the beginning and end of a LONG period of time. Thus, a string of logic zeros may allow a reader to determine the LONG period for that swipe. A logic one may recognized, for example, when a pulse is provided in the middle of a LONG period of time such that the reader sees two SHORT periods of time. Accordingly, changing the time between when a current increase and decrease occurs may be utilized to communicate a logic one or logic zero. Similarly, the amount of time before a current decrease and increase occurs may be utilized to communicate a logic one or a logic zero.

Range 730 may correlate to a current drive signal that swings between a positive and a negative polarity. As a result, the amplitude of sense signal 741 on range 740 may be increased with respect to signal 731 having the same amplitude, but a single polarity.

Figure 8:
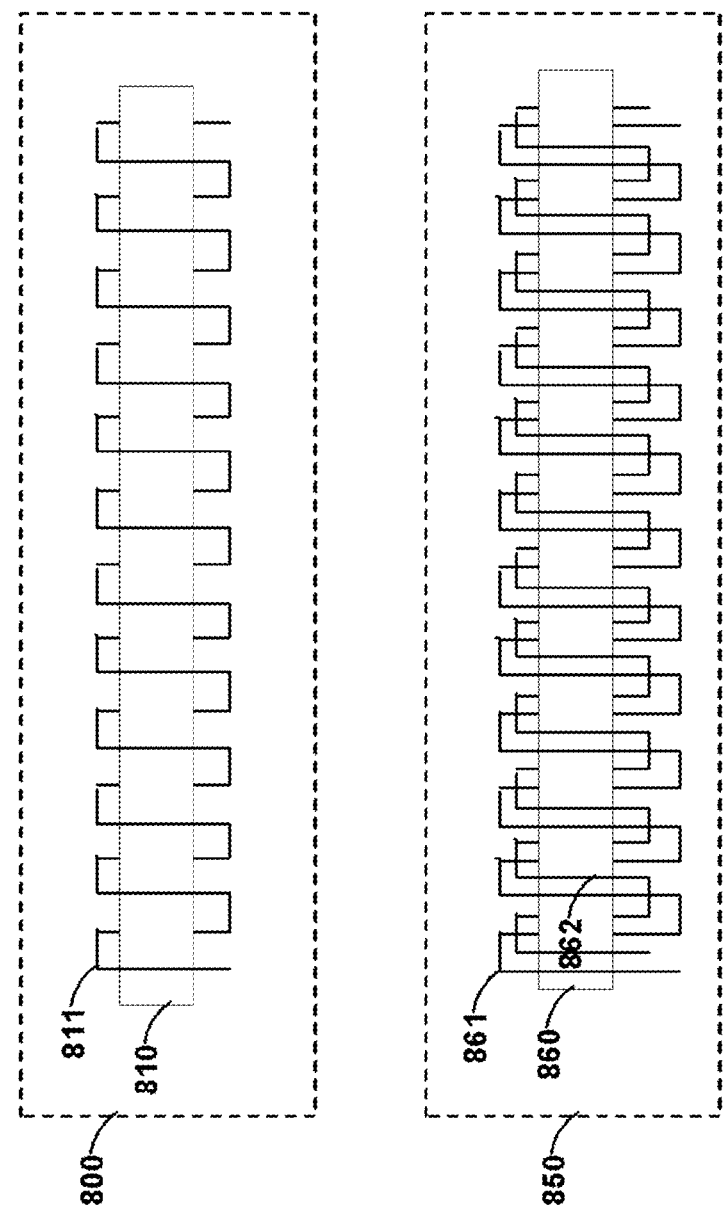
FIG. 8 is an illustration of coils constructed in accordance with the principles of the present invention.

FIG. 8 shows magnetic emulator 800 that may be utilized, for example, to communicate data serially to a magnetic stripe reader. Emulator 800 may include coil 811 around material 810. Material 810 may be, for example, a soft magnetic material.

Magnetic emulator 850 may be utilized, for example, to communicate data serially to a magnetic stripe reader. Emulator 850 may include coil 861 and 862 around material 860. Material 860 may be, for example, a soft magnetic material. Persons skilled in the art will appreciate that the increased number of coil turns may, for example, result in a larger electromagnetic field. Coil 861 may be fabricated on one layer above and one layer below material 860. Coil 862 may be fabricated, for example, on a different layer above and a different layer below material 860.

Figure 9:
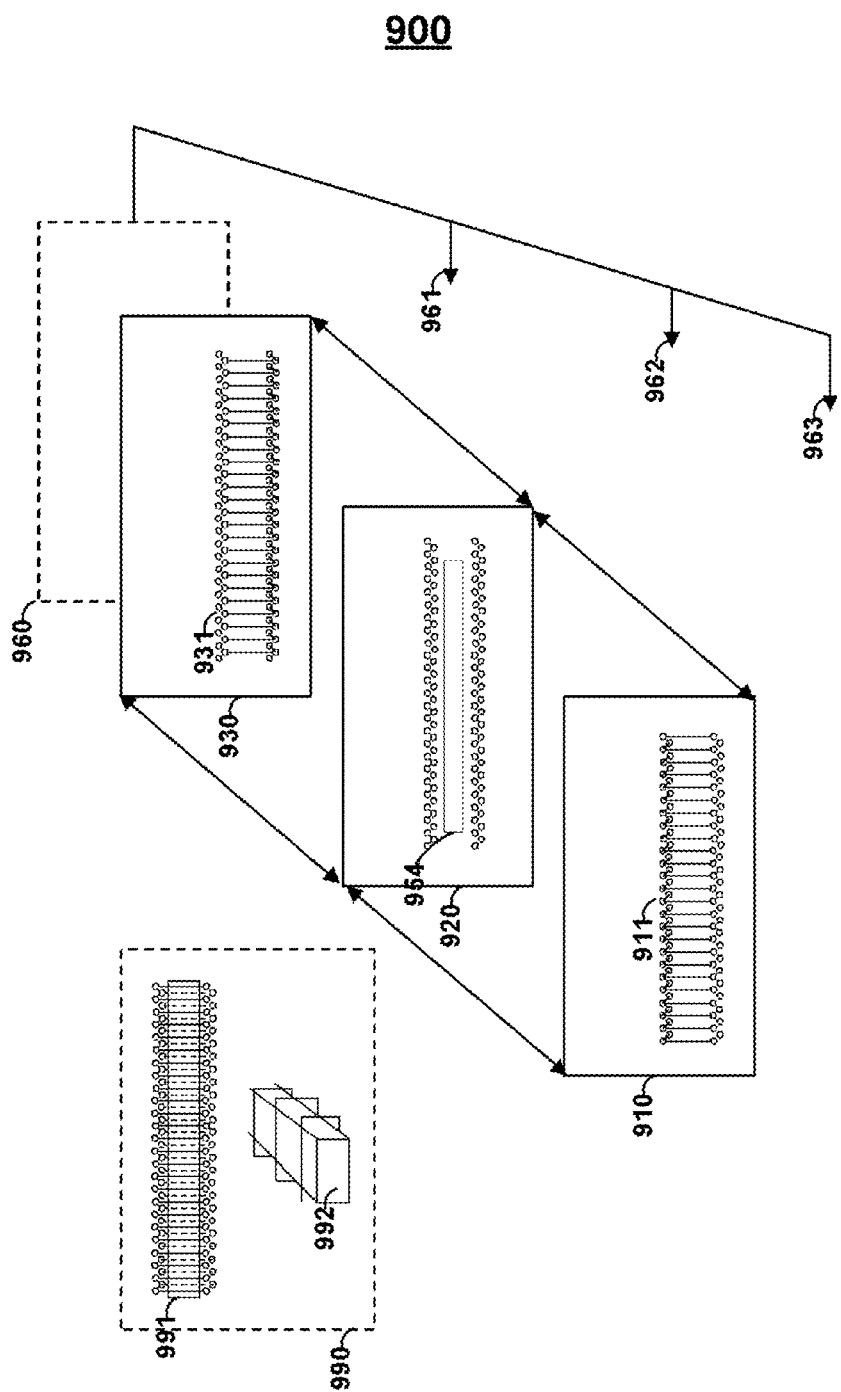
FIG. 9 is an illustration of a card manufacturing process constructed in accordance with the principles of the present invention.

FIG. 9 shows manufacturing process 900 that may be utilized, for example, to provide a card that includes a coil (e.g., coil 990). Coil 990 may take the form of birds-eye view perspective 991 and angled cross-sectional perspective 992.

Layer 910 may be provided. Coil segments 911 may be printed on, for example, layer 910. Material 953 may be provided between layer 910 and layer 930. Material 954 may be provided on layer 920 (e.g., printed on layer 920). Vias may be provided on layer 920 to couple, for example, coil segments 911 to coil segments 931 of layer 930. Additional layers may be provided. For example, layer 910 may be provided and may include printed contacts for interconnecting circuitry. Layer 960 may be provided, for example, at locations 961-963. For example, layer 960 may be provided as shown and at location 963. Each such layer may include, for example, coil segments for a second coil. Layers 910, 920, and 930 may, for example, include vias for coupling the coil segments for the second coil together. Any layer of FIG. 9 may include contacts to, and interconnections between, card components such as a processor, LEDs, buttons, battery, RFID, and IC chip (e.g., EMV chip).

Figure 10:
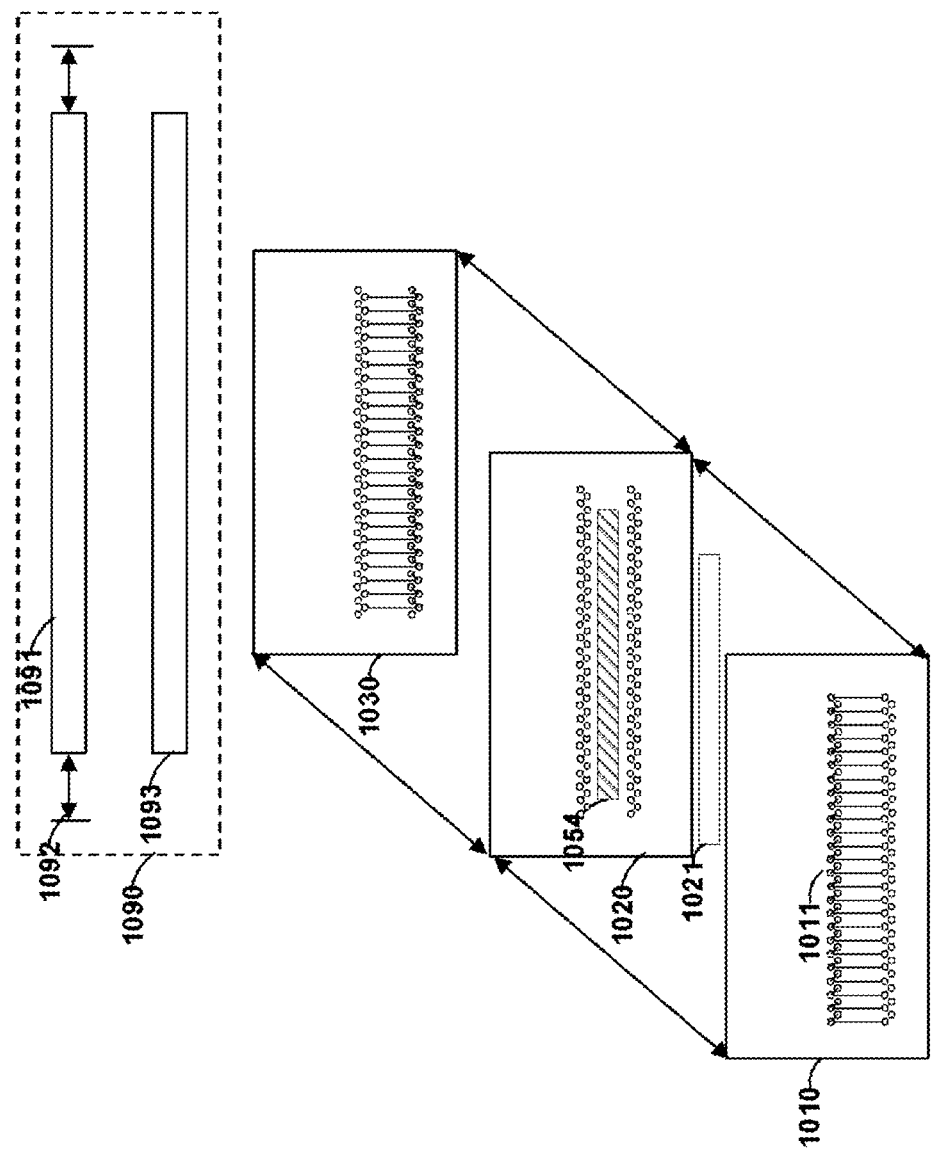
FIG. 10 is an illustration of a card manufacturing process constructed in accordance with the principles of the present invention.

FIG. 10 shows materials 1090 that includes material 1091 and 1093. Material 1091 may be magnetostrictive such that, for example, material 1091 mechanically distorts in the presence of a magnetic field. For example, material 1091 may distort from a resting location to distorted location 1092. Material 1091 may affect an electromagnetic field as material 1091 distorts. Materials 1093 may, for example, be a soft-magnetic material with zero, or substantially zero, parts per million of magnetostriction. Material 1093 may be operable to affect an electromagnetic field without distorting.

Person skilled in the art will appreciate that a magnetostrictive material may, for example, have a better performance if allowed to mechanically distort. Accordingly, for example, layer 1020 may be provided with aperture 1054. Magnetostrictive material 1021 may be placed within cavity 1054 such that magnetostrictive material 1021 may mechanically distort within aperture 1054. Layer 1010 may be provided with coil segments 1011 coupled to vias on layer 1020 to couple the coil segments on layer 1010 to layer 1030.

Figure 11:
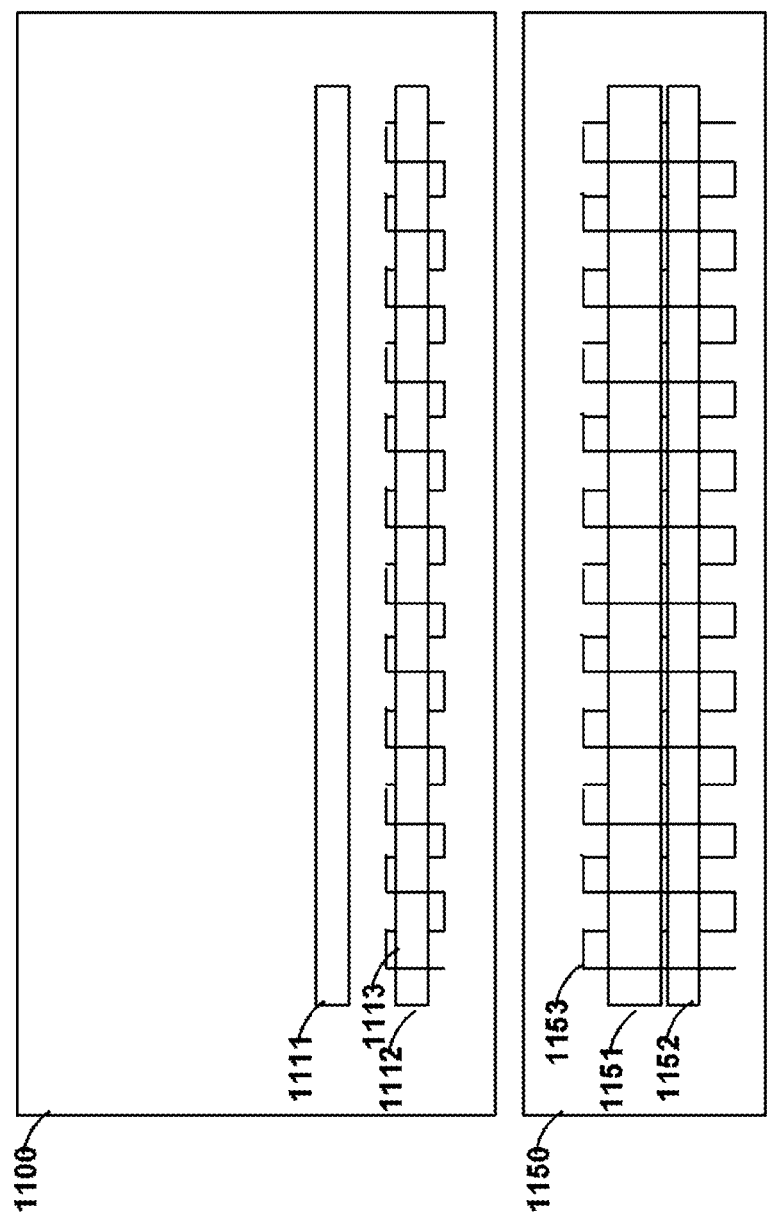
FIG. 11 are illustrations of cards constructed in accordance with the principles of the present invention.

FIG. 11 shows card 1100 that may include, for example, permanent magnet 1111 located about coil 1113. Coil 1113 may be located around material 1112. Material 1112 may be, for example, a soft-magnetic material. Persons skilled in the art will appreciate that permanent magnet 1111 may provide a bias magnetic field that may increase the field located at the exterior of coil 1113 by providing bias to the field located at the exterior of coil 1113.

Cross-section 1150 may be, for example, a cross section of any type of card (e.g., payment card, gambling card, phone card, security access card). Coil 1153 may be provided, for example, to communicate data serially to a magnetic stripe reader. Soft-magnetic material 1151 may be provided within coil 1153. Similarly, for example, permanent magnet 1152 may be provided inside of coil 1153. Soft-magnetic material 1151 may be, for example, thicker (or thinner) than magnet 1152. Similarly, for example, soft magnetic material 1151 may be physically touching permanent magnet 1152 or may be separated (e.g., via an insulator).

Figure 12:
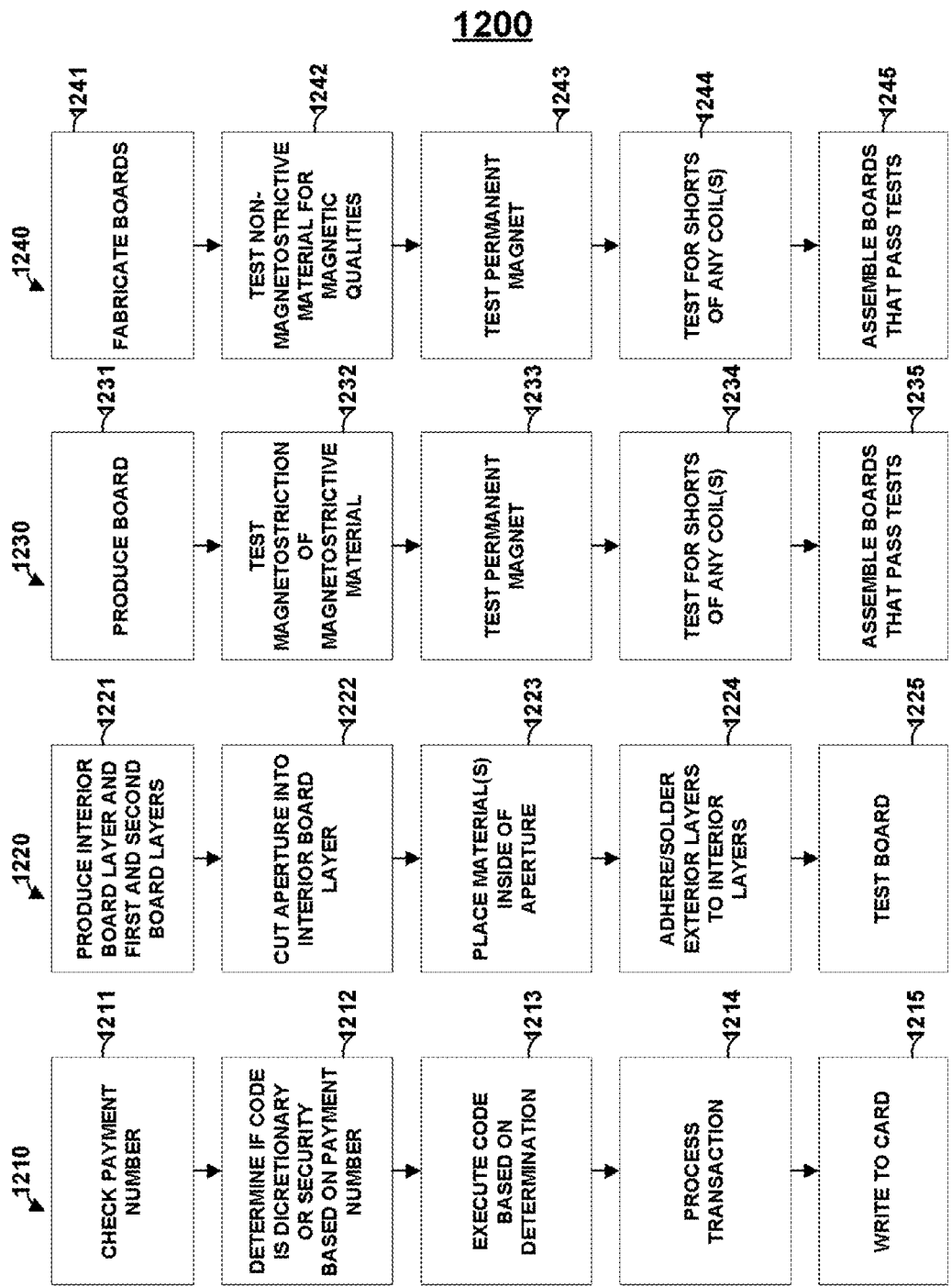
FIG. 12 are flow charts constructed in accordance with the principles of the present invention.

FIG. 12 shows flow charts 1200 that may include, for example, flow chart 1210, 1220, 1230, and 240. Flow chart 1210 may include step 1211, in which a number, such as a payment number, may be retrieved. Step 1213 may determine, for example, whether the payment number is associated with a security code, discretionary code, a code for both security and discretionary data, or no code. The code may be executed in step 1213. For example, if a security code is associated with a payment number then the security code may be, for example, validated. As per another example, if a discretionary code is associated with a payment number then the discretionary code may be, for example, validated. Persons skilled in the art will appreciate that no code may be associated to a payment number or only in particular instances (e.g., online purchases). Similarly, a card may have both a security component and a discretionary data portion. A transaction (e.g., a payment transaction) may be validated in step 1214. Step 1215 may, for example, be included to allow for a device to provide information to a card (e.g., via a magnetic stripe emulator, RFID antenna, or IC chip).

Process 1220 may be provided. Step 1221 may be included in process 1220 that may, for example, include producing an interior and two exterior layers. Such layers may be, for example, a printed circuit board layer (e.g., an FR4 layer). Step 1221 may include, for example, steps such as layer printing, cutting, and testing. Step 1222 may be included to cut, for example, an aperture into the interior board layer. Such an aperture may be sized to approximately the size of one or more materials that may be utilized in the interior of a coil of a magnetic emulator. The aperture may, for example, be larger than the one or more materials utilized in the interior of a coil of a magnetic emulator. Persons skilled in the art will appreciate that such a material may be a magnetostrictive material that distorts in the presence of a magnetic field in order to provide a particular influence on that magnetic field. Accordingly, a magnetostrictive material may be utilized with, for example, a two-dimensional coil (e.g., underneath or above) or another type of device (e.g., a magnetic encoder). Persons skilled in the art will also appreciate, for example, that a magnetostrictive material may distort if the material is placed in a cavity that is the same size as the magnetostrictive material. A magnetostrictive material may be configured to distort, for example, so long as the magnetostrictive material is not adhered to adjacent board layers.

Step 1222 may be utilized to place a material into the aperture. Person skilled in the art will appreciate that an aperture may be cut through a board layer and that a cut may be provided that only provides space partially through a board such that a trough is formed. Any material may be placed in a space that is cut for the material. For example, a permanent magnet or non-magnetostrictive material may be placed in such a space. In doing so, for example, a multiple layer board may be formed that has even exterior surfaces void of bulges. Without a space, for example, a bulge may appear. Bulges may be useful, however, in that apertures may increase the cost of making a multiple layer card. Apertures may also be cut into layers exterior to the layer housing the material (e.g., all layers) in order to reduce bulges as well as provide a thin card. For example, a permanent magnet may be placed outside of a coil and an aperture may be cut through all layers of the multiple layer circuit board such that a relatively thick permanent magnet may be provided. A material and board layer including an aperture may, for example, be configured to have substantially the same thickness. A machine may autonomously cut spaces and place materials into those spaces. Layers of a multiple-layer board may be adhered together in step 1224 and the board may be tested in step 1225.

Process 1230 may be provided in which a single or multiple-layer board (e.g., utilizing FR4) is produced in step 1231. The board may include a magnetostrictive material and the magnetostriction of the magnetostrictive material may be tested in step 1232. The magnetostriction of a material may be tested, for example, by providing a particular amount of current through a coil in which the magnetostrictive material resides and determining the amount of electromagnetic field produced by the magnetostrictive material.

The magnetism associated with a permanent magnetic included in a multiple layer board (if a permanent magnet is provided) may be tested in step 1233. Tests for any shorts, such as shorts in one or more coils, may be tested in step 1234. Boards that pass all tests may be, for example, assembled in step 1235 by placing electrical components (e.g., microprocessors, LEDs, oscillators, buttons, IC chips) on a board. Persons skilled in the art will appreciate that boards for cards may be fabricated in sheets and assembly and lamination may also occur in sheets.

Programming may also be performed while cards are in sheet form as well as any additional personalization (e.g., printing and embossing). Sheets may be cut into cards at any time (e.g., after the cards are ready for mailing).

Process 1240 may be included. A single or multiple layer board may be fabricated in step 1241. Non-magnetostrictive material may be tested in step 1242. Permanent magnets may be tested in step 1243. Magnetostrictive material (if provided on a board) may also be tested. Shorts may be tested for in step 1244 and boards may be assembled or sent to an assembler in step 1245.

Figure 13:
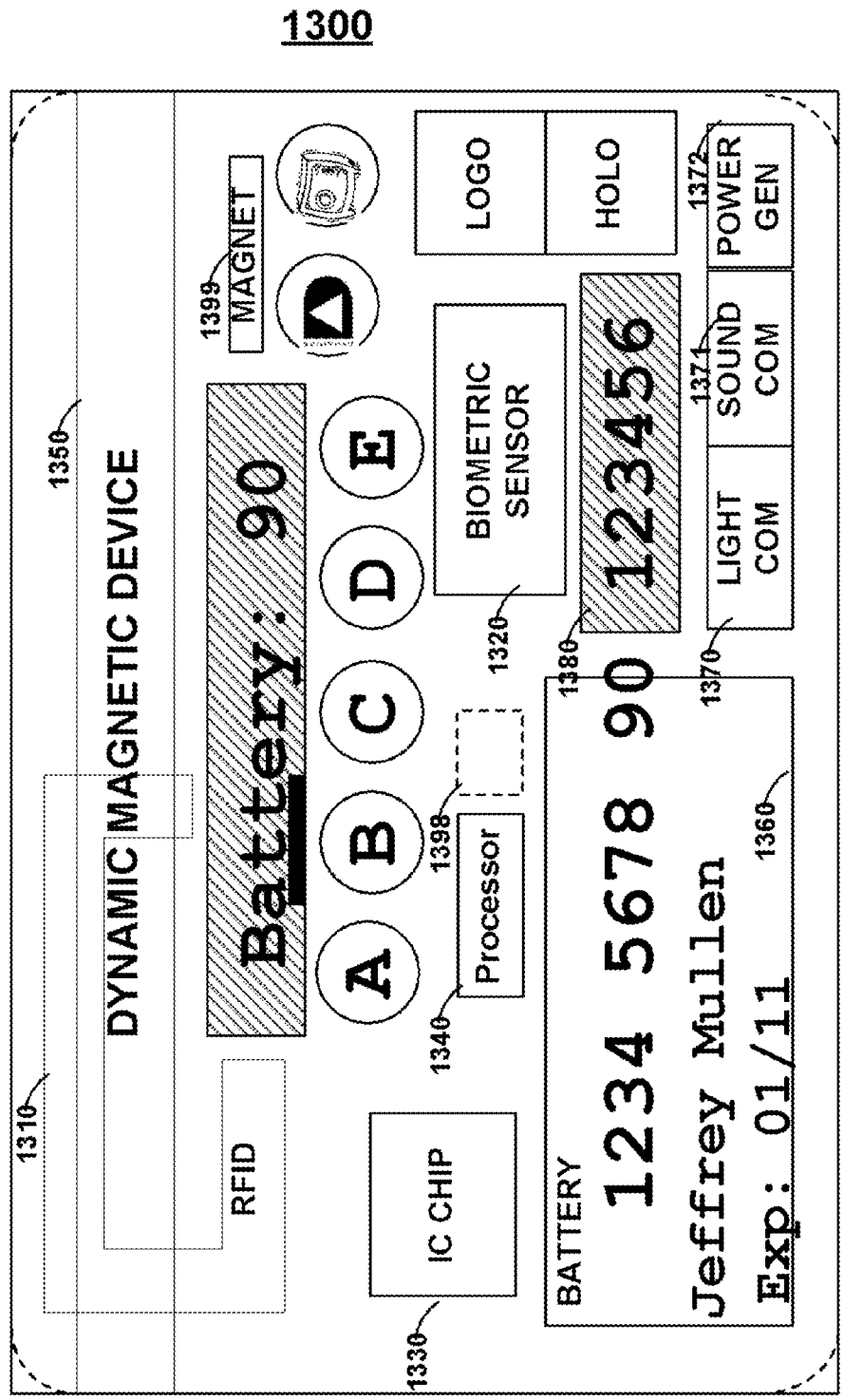
FIG. 13 is an illustration of a card constructed in accordance with the principles of the present invention.

FIG. 13 shows card 1300 that may include a number of components for use in cards such as payment cards. Card 1300 may include RFID 1312, dynamic magnetic device 1350 (which may include one or more magnetic encoders or emulators), IC chip 1330, processor 1340, battery 1360, display 1380, biometric sensor 1320, permanent magnetic 1399, light communications device 1370 (for receiving and/or sending light-based information signals), sound communications device 1371 (for receiving and/or sending sound-based information signals), and power generator 1372 (for generating electrical energy to recharge battery 1360). Persons skilled in the art will appreciate that additional components may be provided on card 1300. For example, an oscillator may be provided as component 1398 such that time may be kept (e.g., to assist the deployment of time-based encryption).

Figure 14:
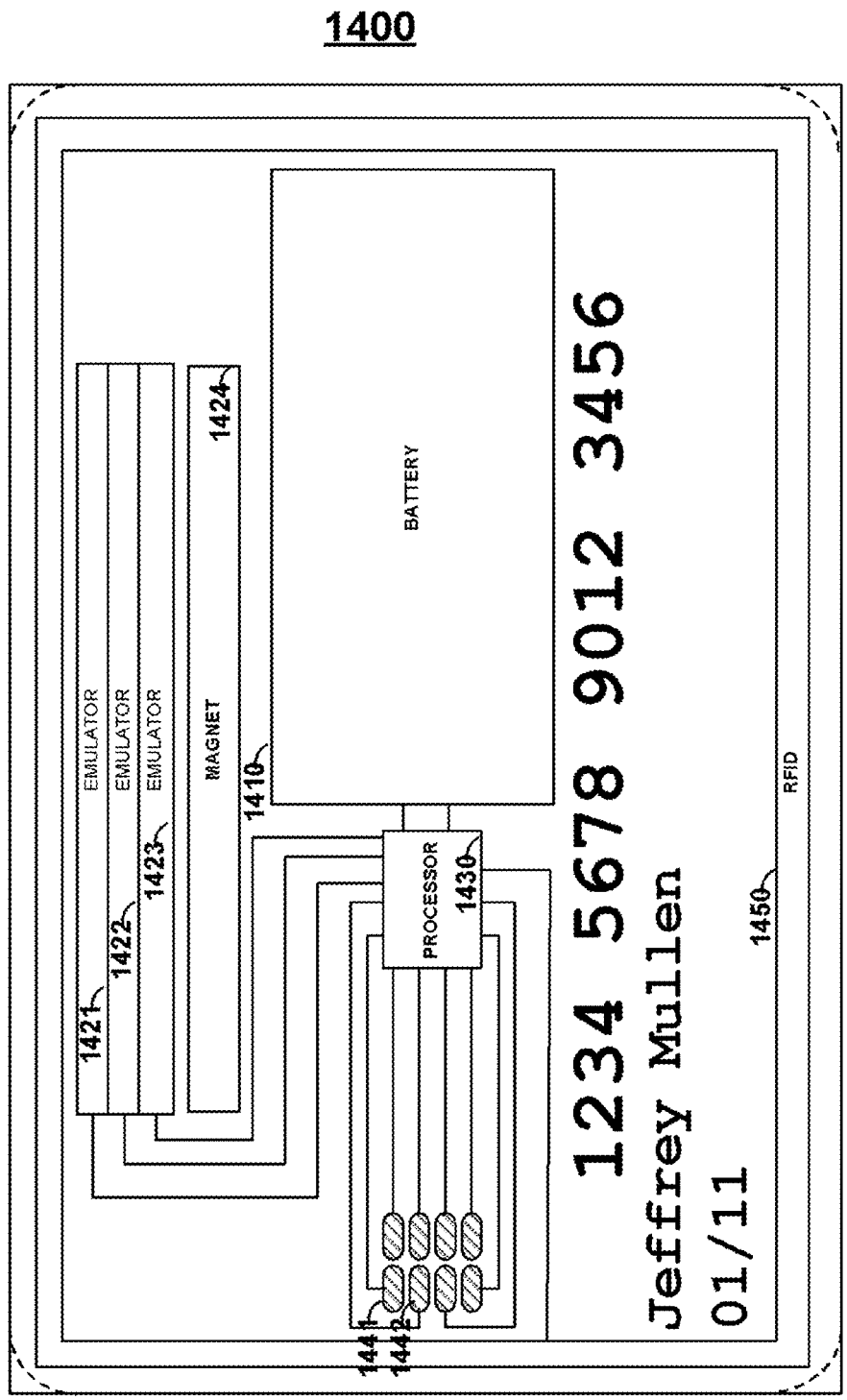
FIG. 14 is an illustration of a card constructed in accordance with the principles of the present invention.

FIG. 14 shows card 1400 that may include, for example, magnetic emulator 1422 (e.g., for serially communicating track 1 information), magnetic emulator 1423 (e.g., for serially communicating track 2 information), and permanent magnet 1424. Persons skilled in the art will appreciate, for example, that a permanent magnet may be configured to provide a bias magnetic field that does not substantially emit from card 1300 such that the bias magnetic field may not substantially affect objects placed outside of card 1400 (e.g., a static magnetic stripe of a nearby payment card). Furthermore, permanent magnet 1424 may be configured such that permanent magnet 1424 is not strong enough to, for example, erase information of any nearby static magnetic stripes. Similarly, the coercivity of such a permanent magnet may be large such that the permanent magnet may have an expected lifespan of a relatively long period of time (e.g., over 10 years).

Card 1400 may include, for example, RFID 1450, battery 1410, processor 1430 and EMV chip contacts 1441 and 1442 such that processor 1430 may perform the processing of an EMV chip such that card 1400 may not include, for example, an EMV chip.

Figure 15:
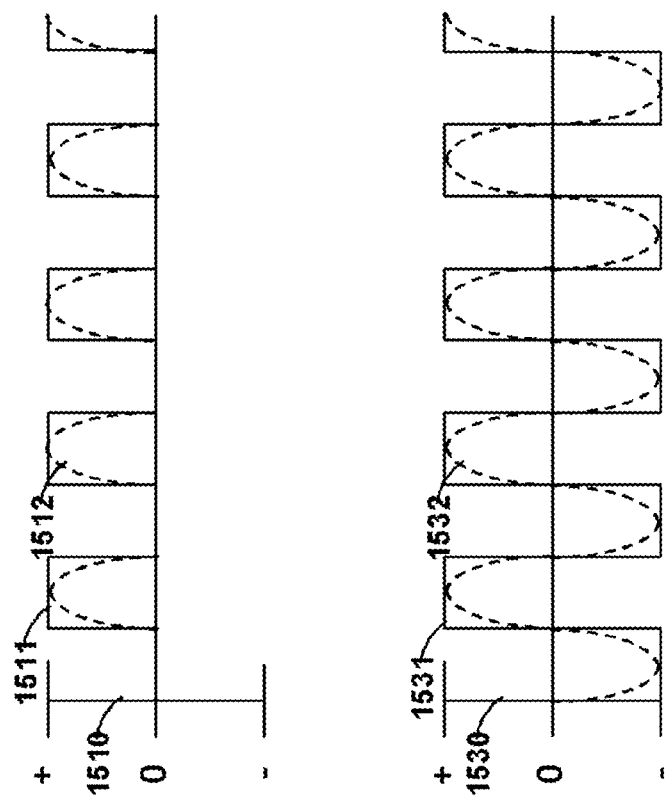
FIG. 15 is an illustration of control signals constructed in accordance with the principles of the present invention

FIG. 15 shows control signals 1500. Range 1500 may include control signal 1512. Persons skilled in the art will appreciate that skewing control signal 1511 to produce curved signal 1512 may increase the ability for a magnetic stripe reader to recognize information. Similarly, range 1530 shows control signal 1531 skewed to provide a curved control signal in both a positive and negative polarity.

Figure 16:
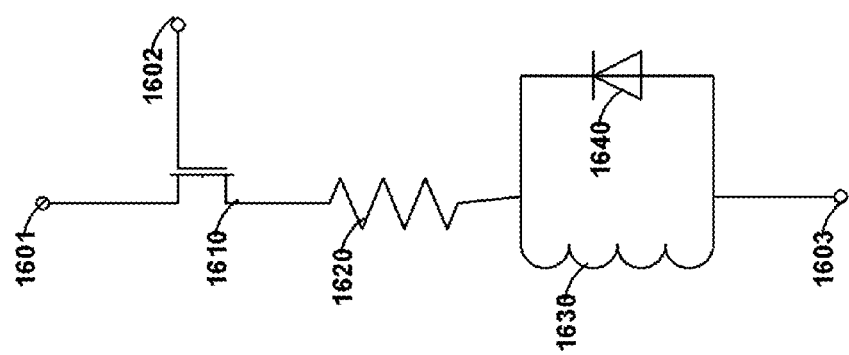
FIG. 16 is a schematic of a drive circuit constructed in accordance with the principles of the present invention.

FIG. 16 shows driving circuit 1600. Driving circuit 1600 may include, for example, node 1601, node 1602, transistor 1610, resistor 1620, coil 1630, diode 1640, and node 1603. Persons skilled in the art will appreciate that a voltage may be coupled to note 1601. A processor may be coupled to, for example, node 1602. processor may control when the voltage coupled to node 1601 is coupled to resistor 1620 via transistor 1610. Resistor 1620 may be utilized, for example, to provide a drive current through coil 1630. Node 1603 may be coupled, for example, to ground. Diode 1640 may be coupled in parallel with coil 1630 in order to, for example, protect against voltage pulses that may be generated as the result of the inductance of coil 1630. Coil 1630 may be provided, for example, without diode 1640.

Figure 17:
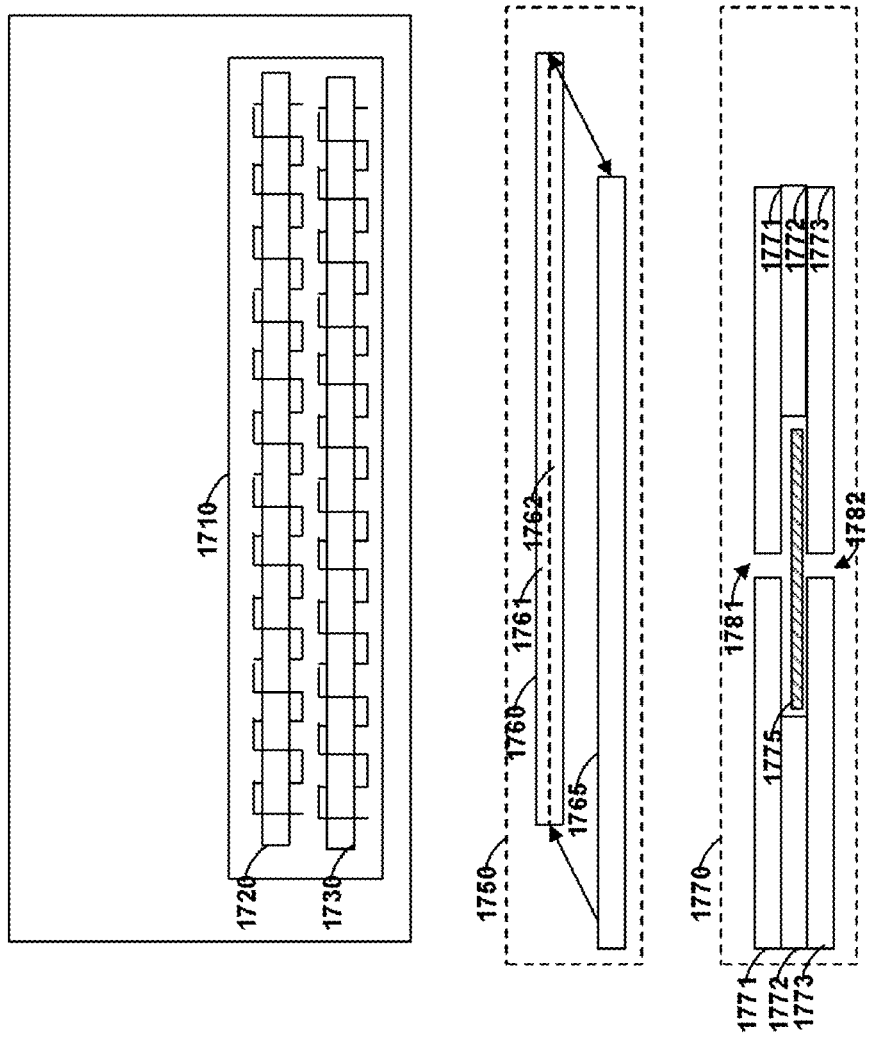
FIG. 17 is an illustration of a card constructed in accordance with the principles of the present invention.

FIG. 17 shows card 1700 that may include emulators 1720 and 1730 located above a surface of permanent magnet 1710. Persons skilled in the art will appreciate that a permanent magnet may be provided above one or more coils and another permanent magnet may be provided below, for example, those one or more coils. Persons skilled in the art will appreciate that a permanent magnet may be polarized and oriented in a number of ways. For example, arrangement 1750 may be provided in which soft-magnetic material 1170 may be provide adjacent to permanent magnet 1760. Permanent magnet 1760 may be polarized such that region 1761 has one pole (e.g., a North pole) and region 1762 has another pole (e.g., a South pole). Persons skilled in the art will appreciate that materials may be polarized to form a permanent magnet. For example, a polarized metal, such as a magnetized steel allow, may be utilized.

Card portion 1770 shows layer 1771, 1772 and 1773. A cavity may be provided, for example, by cutting out a portion of layer 1772. A material (e.g., magnetostrictive material 1775 may be provided in the cavity. Persons skilled in the art will appreciate that, for example, apertures may be provided (e.g., aperture 1781 of layer 1771 and aperture 1782 of layer 1773). Such apertures may, for example, be provided before board layers are adhered together in order to, for example, prohibit a vacuum from forming inside of a cavity. Similarly, for example, apertures may be cut after a board is adhered to remove a vacuum from forming in a cavity. Such apertures may also be utilized to test characteristics of material 1781 as well as an associated device (e.g., a dynamic magnetic communications device). For example, testing probes may be placed in such apertures to determine, for example, if material 1781 shorted to other circuitry. Any number of apertures may be provided in any number of locations. A board having apertures may be, for example, laminated over after testing. For example, a board may be laminated via injection molding.

Persons skilled in the art will appreciate that data may be transferred, such as gift card and/or pre-paid card data, to a card in a variety of ways. For example, a card may be swiped a second time through a magnetic stripe reader that includes a magnetic stripe encoder. A coil on the card may be utilized to receive the information and provide the received information to a processor. In doing so, information may be loaded into the card. Similarly, an IC chip may be utilized to receive data as well as a passive or active RFID. Additionally, one or more microphones may be included to receive audio information that may be representative of data. Accordingly, for example, a user may hold his/her card, or other device, next to a device that is operable to transmit audio via a speaker (e.g., laptop, stationary computer, or mobile telephonic device). The audio information may be discerned by the card and utilized to load information into the card (e.g., a gift card or pre-paid card. An application may also be loaded that enhances the functionality of the card. Such an application may include, for example, a user's medical information such that medical information can be displayed via the card (or other device) during a medical emergency. Accordingly, applications and/or payment cards may be purchased online and a speaker may communicate information to a card. Similarly, the card may include a speaker for transmitting information such that bi-directional communications are established. A light detector may be provided on a card that may receive light pulses indicative of data. Accordingly, for example, a user may hold a card up to a display—such as the screen of a laptop, stationary computer, or mobile phone— and information may be communicated from the display to the card via the light detector. Similarly, a light source may be utilized to communicate information from one device to another. For example, a light source (e.g., LED) may be utilized to communicate information from one card to another. Similarly, a magnetic stripe reader may include a light source. A card may be positioned over the light source such that a light detector of the card is aligned with the light source to receive light. Accordingly, the light of a magnetic stripe reader (or other type of reader) may be utilized to communicate information back to a card. A user may utilize interfaces on the card (e.g., buttons) to initiate a transfer of data from one card to another card or from a device to a card. A variety of types of data may be communicated. For example, money may be communicated from one debit card to another debit card such that payments may occur between the cards. Accordingly, for example, the next time a card is utilized via a reader (e.g., a magnetic stripe reader) information of the transfer may be communicated to a server for processing. Light may be utilized to transfer data from a card to a computer using, for example, a camera (e.g., webcam) on the computer. Sound may be utilized to transfer data from a card to a computer using, for example, a microphone on the computer.

A display may also be utilized as an interface. For example, a display may include a contact and an electronic ink. The electronic ink may change colors in response to, for example, a particular electrical signal being supplied to the contact. A capacitive sensor may be coupled to such a contact, however, such that a user interaction with the contact may be sensed by the capacitive sensor. Accordingly, a card may include a display that can also receive user input. Persons skilled in the art will appreciate that a display may include multiple contacts. For example, a display may include multiple 7-segment (e.g., to display digits) or 11-segment, 14-segment, or 16-segment (e.g., to display alphanumerics) regions where each segment may be coupled to a capacitive sensor.

A biometric sensor may be placed on a card or other device. Such a biometric sensor may be, for example, a fingerprint reader. Accordingly, one or more fingerprints may be stored in the memory of a card and compared to scanned fingerprints. Different fingerprints may activate the card differently (e.g., utilize a different user's payment card info).

Persons skilled in the art will appreciate that a user's payment card number (e.g., credit card or debit card number) does not have to change. A display may hide this payment card number until an appropriate unlocking code is entered into buttons of the card. Similarly, a magnetic emulator may not be provided current until the proper unlocking code is entered—thus keeping magnetic information private and not allowing undesirable readers to read a card. A security code may be displayed on the same or a different display. A button may be provided representative of an online purchase (or a user may utilize buttons to instruct the processor that an online purchase is desirable). For such an online purchase, the credit card number and the security code may be displayed— but the magnetic emulator may not be activated. In doing so, the level of security of the card is increased. Furthermore, for example, a button may be provided representative of in-store purchases (or a user may utilize buttons to instruct the processor that an in-store purchase is desirable). Accordingly, a processor may be signaled that an in-store purchase is desired. A different operation may be associated with different types of purchases (e.g., online or in-store). Accordingly, for example, magnetic emulators may be activated for an in-store environment—but not the displays. Accordingly, for example, a restaurant cashier may not be able to read the credit card number from the card, but may still be able to swipe the card. If a reader is down or a cashier requires reading particular information (e.g., a security code or credit card number information) then controls may be utilized to communicate this information. A record of the types of transactions may be stored and may be communicated in discretionary fields of data within a transmitted data track. Such record information may be utilized, for example, to further increase security and/or introduce a variety of additional functionality.

Different types of cards may be provided on a card. For example, a security ID number and a credit card number may both be provided on the same card. A button may be utilized to allow a user to provide instruction to a processor such that the processor can display (e.g., visually and/or magnetically) the desired information. For example, a user may determine to use one of a variety of payment accounts (e.g., credit and/or debit) for a purchase. An entire payment number (e.g., credit or debit) may be changed and/or hidden visually and/or magnetically. A portion of a payment card number (e.g., credit or debit) may be changed and/or hidden visually and/or magnetically.

Persons skilled in the art will appreciate that a display on the card may display a credit card number that does not change with time (or transaction or button press). Additionally, for example, a magnetic emulator (or multiple magnetic emulators) may magnetically communicate financial data that does not change with time. Such a card may reduce, for example, the effects of physical card theft and card cloning.

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipt may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICs may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICs before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICs based, for example, on time or the number of previous unlock attempts.

Figure 18:
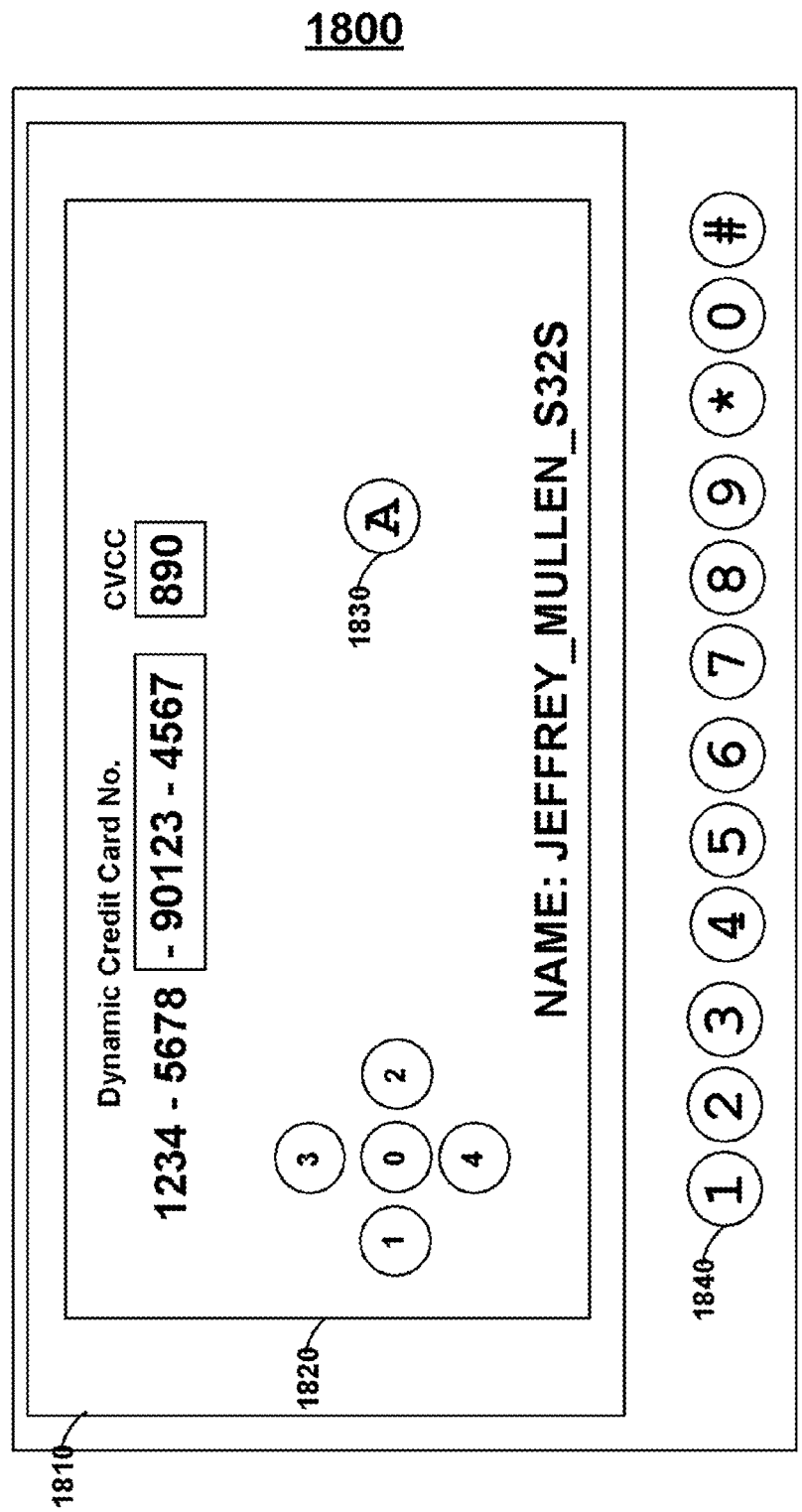
FIG. 18 is an illustration of a personal electronic device constructed in accordance with the principles of the present invention.

FIG. 18 shows personal electronic device 1800 which may be, for example, a portable telephonic device, portable media player, or any type of electronic device. Persons skilled in the art will appreciate that the functionality of a card may be provided on a personal device and displayed through a graphical user interface. Personal electronic device 1800 may include, for example, user inputs 1840 and display 1810. Virtual card 1820 may be displayed on display 1820. Display 1820 may be a touch-sensitive display such that, for example, virtual button 1830 may be provided on virtual card 1820. Persons skilled in the art will appreciate that cards may be provided as virtual cards and a user may interact with such virtual cards in order to provide a variety of functions. Personal electronic device 1800 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A payment card comprising:
    a battery;
    at least one button;
    a magnetic emulator provided on multiple layers of a flexible multiple layer printed circuit board, operable to communicate information to a magnetic stripe reader, generating an electromagnetic signal; and
    a magnet located outside of said magnetic emulator for providing magnetic bias to said electromagnetic signal.

2. The payment card of claim 1, wherein said magnetic emulator includes a coil and a soft-magnetic material is located inside of said coil.

3. The payment card of claim 1, further comprising a display.

4. The payment card of claim 1, wherein said magnetic emulator includes a coil, a soft-magnetic material is located inside of said coil, and said soft-magnetic material is located in a cavity.

5. The payment card of claim 1, further comprising a microprocessor.

6. The payment card of claim 1, wherein said magnetic emulator includes a coil, a soft-magnetic material is located inside of said coil, and said soft-magnetic material is thinner than said magnet.

7. The payment card of claim 1, further comprising an H-bridge.

8. The payment card of claim 1, further comprising:
    a material affecting said electromagnetic signal,
    wherein said multiple layers include at least a first layer, a second layer and a third layer,
    a plurality of first coil segments are on said first layer,
    a plurality of vias are on said second layer, and
    a plurality of second coil segments are on said third layer.

9. The payment card of claim 1, wherein at least one of said multiple layers includes at least one of a contact to at least one of said battery and said button, and an interconnection to at least one of said battery and said button.

10. The payment card of claim 1, wherein said magnetic emulator includes a plurality of coils.

11. The payment card of claim 1, further comprising:
    a magnetostrictive material affecting said electromagnetic signal.

12. The payment card of claim 1, further comprising:
    a magnetostrictive material,
    wherein said multiple layers include at least a first layer, a second layer and a third layer,
    said second layer is between said first layer and said third layer, and
    said second layer includes said magnetostrictive material and an aperture.

13. The payment card of claim 1, further comprising:
    a magnetostrictive material,
    wherein said multiple layers include at least a first layer, a second layer and a third layer,
    said second layer is between said first layer and said third layer, and
    said magnetostrictive material and an aperture are on said second layer, said magnetostrictive material being operable to mechanically distort within said aperture.

14. The payment card of claim 1, further comprising:
    a magnetostrictive material within a cavity.

15. The payment card of claim 1, further comprising:
    a soft-magnetic material,
    wherein said multiple layers include at least a first layer, a second layer and a third layer,
    said second layer is between said first layer and said third layer, and
    said soft-magnetic material is on said second layer.

16. The payment card of claim 1, further comprising:
    a soft-magnetic material with a magnetostriction of about zero,
    wherein said multiple layers include at least a first layer, a second layer and a third layer, said second layer is between said first layer and said third layer, and
said soft-magnetic material is on said second layer.

17. The payment card of claim 1, wherein said magnet is located about said magnetic emulator.

18. The payment card of claim 1, wherein said multiple layers, said magnet and said magnetic emulator extend in parallel in a first direction, and
said magnet is on a side of said magnetic emulator in a second direction perpendicular to said first direction, said second direction not in parallel with said multiple layers, said magnet and said magnetic emulator.

19. The payment card of claim 1, further comprising:
a second magnet;
wherein said multiple layers, said magnets and said magnetic emulator extend in parallel in a first direction, and
said magnets are on opposite sides of said magnetic emulator from each other in a second direction perpendicular to said first direction, said second direction not in parallel with said multiple layers, said magnets and said magnetic emulator.

20. The payment card of claim 1, wherein a length of said magnet is about a length of said magnetic emulator, and
said magnet is in parallel with said magnetic emulator.

21. The payment card of claim 1, wherein said magnetic emulator includes at least one coil, and
said magnet is in parallel with said coil.

22. The payment card of claim 1, further comprising:
a soft-magnetic material,
wherein said multiple layers include at least a first layer, a second layer and a third layer,
a plurality of first coil segments are on said first layer,
a plurality of vias and said soft magnetic material are on said second layer,
a plurality of second coil segments are on said third layer,
said vias each include a connector coupling said first coil segments to said second coil segments, and
said magnetic emulator, said magnet and said soft magnetic material extend in parallel.

23. The payment card of claim 1, further comprising:
a soft-magnetic material within said magnetic emulator,
wherein said soft-magnetic material is in contact with said magnet.

24. The payment card of claim 1, further comprising:
a soft-magnetic material within said magnetic emulator,
wherein said soft-magnetic material is separated from said magnet by an insulator.

25. The payment card of claim 1, further comprising a soft-magnetic material in said magnetic emulator,
wherein said multiple layers include at least a first layer, a second layer and a third layer,
said second layer is between said first layer and said third layer,
said second layer includes an aperture, and
said soft-magnetic material is in said aperture.

26. A payment card comprising:
at least one button;
a magnetic emulator, operable to communicate information to a magnetic stripe reader, for generating an electromagnetic signal, said magnetic emulator comprising:
a coil having an interior and an exterior that is provided on multiple layers of a flexible multiple layer printed circuit board; and
a material placed within a cavity of said multiple layer printed circuit board and said cavity is located in said interior of said coil for increasing the amount of said electromagnetic signal located about said exterior of said coil.

27. The payment card of claim 26, further comprising a display.

28. The payment card of claim 26, further comprising a battery.

29. The payment card of claim 26, further comprising an H-bridge.

30. The payment card of claim 26, further comprising a processor.

31. The payment card of claim 26, wherein said magnetic emulator is provided on multiple layers of a flexible multiple layer printed circuit board.

32. The payment card of claim 26, wherein said multiple layers include at least three layers.

33. The payment card of claim 26, wherein said multiple layers include at least a first layer, a second layer and a third layer,
a plurality of first coil segments are on said first layer,
a plurality of vias are on said second layer, and
a plurality of second coil segments are on said third layer.

34. The payment card of claim 26, further comprising:
at least one card component,
wherein at least one of said multiple layers includes at least one of contacts to said card component and interconnections to said card component.

35. The payment card of claim 26, further comprising:
at least one card component,
wherein at least one of said multiple layers includes at least one of contacts to said card component and interconnections to said card component, and
said card component is at least one of a processor, a light emitting diode, an RFID and an EMV chip.

36. A payment card comprising:
a magnetic emulator, operable to communicate information to a magnetic stripe reader, for providing an electromagnetic signal, wherein said magnetic emulator comprises:
a coil having an interior and an exterior that is provided on multiple layers of a flexible multiple layer printed circuit board;
a material placed within said interior of said coil for increasing the amount of said electromagnetic signal located about said exterior of said coil; and
a magnet placed within the proximity of said coil for providing a bias signal.

37. The payment card of claim 36, wherein a code is communicated via said electromagnetic signal and displayed on said display.

38. The payment card of claim 36, wherein a code is communicated via said electromagnetic signal and said code is time-based.

39. The payment card of claim 36, wherein a code is communicated via said electromagnetic signal and said code is use-based.

40. The payment card of claim 36, wherein said emulator was fabricated on printed circuit board and a property of said material was tested after manufacturing of said printed circuit board.

41. The payment card of claim 36, wherein said magnetic emulator is provided on multiple layers of a flexible multiple layer printed circuit board.

42. The payment card of claim 36, wherein said material is a soft magnetic material and said soft-magnetic material is thinner than said magnet.

43. The payment card of claim 36, wherein said multiple layers include at least a first layer, a second layer and a third layer,
    a plurality of first coil segments are on said first layer,
    vias are on said first layer, said second layer, and said third layer,
    a plurality of second coil segments are on said third layer, and
    said vias include connectors coupling said first coil segments to said second coil segments.

44. The payment card of claim 36, wherein said multiple layers include at least a first layer, a second layer and a third layer,
    said first layer, said second layer and said third layer are each an FR4 layer,
    a plurality of first coil segments are on said first layer,
    said second layer includes an aperture,
    a plurality of second coil segments are on said third layer,
    a plurality of vias extend through said second layer, and
    said vias each include a connector coupling at least one of said first coil segments to at least one of said second coil segments.

45. The payment card of claim 36, further comprising a second magnet.

46. The payment card of claim 36, wherein said magnetic emulator is a plurality of magnetic emulators, and
    said card is configured such that said bias signal does not substantially affect objects external to said card.

47. The payment card of claim 36, wherein a magnitude of a coercivity of said magnet corresponds to an expected magnet lifespan of greater than about 10 years.

\* \* \* \* \*